US011236058B2

(12) United States Patent
Yan et al.

(10) Patent No.: US 11,236,058 B2
(45) Date of Patent: *Feb. 1, 2022

(54) COMPOUNDS, COMPOSITIONS AND METHODS FOR TREATING OR PREVENTING A SYMPTOM ASSOCIATED WITH GOUT OR HYPERURICEMIA

(71) Applicant: ARTHROSI THERAPEUTICS, INC., Laguna Hills, CA (US)

(72) Inventors: Shunqi Yan, Laguna Hills, CA (US); Li-Tain Yeh, Laguna Hills, CA (US); Robert Orr, Laguna Hills, CA (US)

(73) Assignee: ARTHROSI THERAPEUTICS, INC., Laguna Hills, CA (US)

( * ) Notice: Subject to any disclaimer, the term of this patent is extended or adjusted under 35 U.S.C. 154(b) by 153 days.

This patent is subject to a terminal disclaimer.

(21) Appl. No.: 16/684,046

(22) Filed: Nov. 14, 2019

(65) Prior Publication Data

US 2020/0148659 A1 May 14, 2020

Related U.S. Application Data

(63) Continuation of application No. 16/268,367, filed on Feb. 5, 2019, now Pat. No. 10,508,093, which is a continuation of application No. 16/151,641, filed on Oct. 4, 2018, now Pat. No. 10,239,854, which is a continuation of application No. PCT/US2017/041763, filed on Jul. 12, 2017.

(60) Provisional application No. 62/363,473, filed on Jul. 18, 2016.

(51) Int. Cl.
*C07D 307/80* (2006.01)
*A61P 19/06* (2006.01)
*A61K 45/06* (2006.01)

(52) U.S. Cl.
CPC ............ *C07D 307/80* (2013.01); *A61K 45/06* (2013.01); *A61P 19/06* (2018.01); *C07B 2200/05* (2013.01)

(58) Field of Classification Search
CPC ........ C07D 307/80; A61P 19/06; A61K 45/06
USPC ....................................................... 514/469
See application file for complete search history.

(56) References Cited

U.S. PATENT DOCUMENTS

| | | | |
|---|---|---|---|
| 4,327,725 A | 5/1982 | Cortese et al. | |
| 4,624,848 A | 11/1986 | Lee | |
| 4,968,509 A | 11/1990 | Radebaugh et al. | |
| 5,323,907 A | 6/1994 | Kalvelage | |
| 5,456,923 A | 10/1995 | Nakamichi et al. | |
| 5,461,140 A | 10/1995 | Heller et al. | |
| 5,516,527 A | 5/1996 | Curatolo | |
| 5,622,721 A | 4/1997 | Dansereau et al. | |
| 5,686,105 A | 11/1997 | Kelm et al. | |
| 5,700,410 A | 12/1997 | Nakamichi et al. | |
| 5,977,175 A | 11/1999 | Lin | |
| 6,465,014 B1 | 10/2002 | Moroni et al. | |
| 6,932,983 B1 | 8/2005 | Straub et al. | |
| 10,239,854 B2 | 3/2019 | Yan et al. | |
| 10,508,093 B2 | 12/2019 | Yan et al. | |
| 2007/0185195 A1 | 8/2007 | Endou et al. | |
| 2008/0305169 A1 | 12/2008 | Miki et al. | |
| 2012/0184587 A1 | 7/2012 | Kobashi et al. | |
| 2013/0225673 A1 | 8/2013 | Wempe et al. | |
| 2014/0128460 A1 | 5/2014 | Hegde | |
| 2014/0357683 A1* | 12/2014 | Gunawardhana | A61K 31/426 514/365 |
| 2015/0031768 A1 | 1/2015 | Groves et al. | |
| 2016/0031879 A1 | 2/2016 | Karra et al. | |
| 2017/0349562 A1 | 12/2017 | Hegde | |

FOREIGN PATENT DOCUMENTS

| | | |
|---|---|---|
| CN | 104262305 A | 1/2015 |
| CN | 104311516 A | 1/2015 |
| DE | 19624292 A1 | 1/1998 |
| JP | 2010525081 A | 7/2010 |
| JP | 2013539757 A | 10/2013 |
| WO | WO-2012048058 A2 | 4/2012 |
| WO | WO-2015134467 A1 | 9/2015 |
| WO | WO-2018017368 A1 | 1/2018 |
| WO | WO-2020118113 A1 | 6/2020 |
| WO | WO-2020118114 A1 | 6/2020 |

OTHER PUBLICATIONS

Arnold et al. Liquid chromatography-mass spectrometry in metabolic research. I. Metabolites of benzbromarone in human plasma and urine. Journal of Chromatography 554(1-2):267-80 (1991).
Cho et al. Identification of novel glutathione adducts of benzbromarone in human liver microsomes. Drug Metabolism and Pharmacokinetics 32(1):46-52 (2017).
De Vries et al. Benzbromarone hydroxylation in man: defective formation of the 6-hydroxybenzbromarone metabolite. The Clinical investigator 71(11):947-52 (1993).
De Vries et al. Metabolism of benzbromarone in man: structures of new oxidative metabolites, 6-hydroxy- and 1'-oxo-benzbromarone, and the enantioselective formation and elimination of 1'-hydroxybenzbromarone. Xenobiotica 23(12):1435-50 (1993).
De Vries et al. The isolation, identification and structure of a new hydroxylated metabolite of benzbromarone in man. Xenobiotica 19(12):1461-70 (1989).
Iwamura et al. CYP2C9-mediated metabolic activation of losartan detected by a highly sensitive cell-based screening assay. Drug Metab Dispos 39(5):838-846 (2011).
Kitagawara et al. Novel Bioactivation Pathway of Benzbromarone Mediated by Cytochrome P450. Drug Metab Dispos 43:1303-1306 (2015).

(Continued)

*Primary Examiner* — Yevgeny Valenrod
(74) *Attorney, Agent, or Firm* — Wilson Sonsini Goodrich & Rosati

(57) ABSTRACT

The inventive subject matter provides compounds, compositions and methods for lowering serum acid (sUA) for the treatment of gout, and having reduced liver toxicity, associated with CYP2C9 metabolic pathway.

9 Claims, No Drawings

(56) References Cited

OTHER PUBLICATIONS

Kobayashi et al. Cytotoxic effects of benzbromarone and its 1'-hydroxy metabolite in human hepatocarcinoma FLC4 cells cultured on micro-space cell culture plates. Drug metabolism and pharmacokinetics 28(3):265-8 (2013).
Kobayashi et al. Identification of CYP isozymes involved in benzbromarone metabolism in human liver microsomes. From Biopharmaceutics & Drug Disposition 33(8):466-473 (2012).
Lee et al. A benefit-risk assessment of benzbromarone in the treatment of gout. Was its withdrawal from the market in the best interest of patients? Drug Safety 31 (8):643-665 (2008).
Locuson et al. Charge and Substituent Effects on Affinity and Metabolism of Benzbromarone-Based CYP2C19 Inhibitors. J Med Chem 47(27):6768-6776 (2004).
Maurer et al. Urinary metabolites of benzbromarone in man. Arzneimittel-Forschung 40(4):460-2 (1990).
McDonald et al. Sequential Metabolism and Bioactivation of the Hepatotoxin Benzbromarone: Formation of Glutathione Adducts From a Catechol Intermediate. Chem Res. Toxicol 20:1833-1842 (2007).
PCT/US2017/041763 International Search Report and Written Opinion dated Oct. 20, 2017.
SciFinder Search 2018 (358 pages).
U.S. Appl. No. 16/268,367 Office Action dated May 9, 2019.
Uchida et al. Benzbromarone Pharmacokinetics and Pharmacodynamics in Different Cytochrome P450 2C9 Genotypes. Drug Metab Pharmacokinet 25(6):605-610 (2010).
Walter-Sack et al. Biliary excretion of benzbromarone and its hydroxylated main metabolites in humans. European Journal of Medical Research 3(1/2):45-49 (1998).
Walter-Sack et al. Rapid and slow benzbromarone elimination phenotypes in man: benzbromarone and metabolite profiles. European Journal of Clinical Pharmacology 39(6):577-81 (1990).
Wu et al. Metabolism studies of benzbromarone in rats by high performance liquid chromatography-quadrupole time of flight mass spectrometry. Journal of Chromatography B: Analytical Technologies in the Biomedical and Life Sciences 911:122-132 (2012).
PCT/US2019/064784 International Search Report and Written Opinion dated Feb. 25, 2020.
PCT/US2019/064785 International Search Report and Written Opinion dated Feb. 25, 2020.
Bush et al. Substrate probes for the mechanism of aromatic hydroxylation catalyzed by cytochrome p. 450: selectively deuterated analogs of warfarin. Journal of medicinal chemistry 28.8:992-996 (1985).
Darbyshire et al. Substrate probe for the mechanism of aromatic hydroxylation catalyzed by cytochrome P450. Drug metabolism and disposition 24(9):1038-1045 (1996).
Gannett et al. Synthesis of deuterated naproxens. Journal of Labelled Compounds and Radiopharmaceuticals: The Official Journal of the International Isotope Society 50(14):1272-1275 (2007).
Heimark et al. The synthesis of deuterium labelled metabolites of warfarin and phenprocoumon. Journal of Labelled Compounds and Radiopharmaceuticals 23(2):137-148 (1986).
Leroy et al. Synthesis of deuterium-labelled diclofenac sodium. Journal of Labelled Compounds and Radiopharmaceuticals 33(11):1019-1027 (1993).
Waterhouse. Synthesis of deuterium labelled 4'-hydroxydiclofenac. Journal of Labelled Compounds and Radiopharmaceuticals: The Official Journal of the International Isotope Society 42(11):1075-1083 (1999).
Wu et al. Synthesis of deuterium labelled 4'-hydroxy diclofenac with improved isotopic enrichment. Journal of labelled compounds and radiopharmaceuticals. 52(13):535-537 (2009).
Bernstein. Crystal Structure Prediction and Polymorphism. ACA Transactions 39:14-23 (2004).
Braga et al. Making crystals from crystals: a green route to crystal engineering and polymorphism. J. Royal Soc. Chem. Commun 29:3635-3645 (2005).
International Conference on Harmonization of Technical Requirements for Registration of Pharmaceuticals for Human Use (ICH), "Impurities: Guidelines for Residual Solvents Q3C(R6)." (Oct. 2016).
Jones et al. Pharmaceutical Cocrystals: An Emerging Approach to Physical Property Enhancement. MRS Bulletin 31:875-879 (2006).
Liberman et al. Pharmaceutical Dosage Forms. 2nd Ed. 1:209-214 (1990).
Price. The computational prediction of pharmaceutical crystal structures and polymorphism. Advanced Drug Delivery Reviews 56:301-319 (2004).
Singh et al. Encyclopedia of Pharmaceutical Technology 2nd Ed. pp. 751-753 (2002).

* cited by examiner

COMPOUNDS, COMPOSITIONS AND METHODS FOR TREATING OR PREVENTING A SYMPTOM ASSOCIATED WITH GOUT OR HYPERURICEMIA

This application is a continuation of application Ser. No. 16/268,367, filed Feb. 5, 2019, which is a continuation of application Ser. No. 16/151,641, filed Oct. 4, 2018, now U.S. Pat. No. 10,239,854, issued Mar. 26, 2019, which is a continuation of International Application No. PCT/US2017/041763, filed on Jul. 12, 2017, entitled "COMPOUNDS, COMPOSITIONS AND METHODS FOR TREATING OR PREVENTING A SYMPTOM ASSOCIATED WITH GOUT OR HYPERURICEMIA", which claims the benefit of priority to U.S. provisional patent application No. 62/363,473, filed on Jul. 18, 2016. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is compounds, compositions and methods for treating or preventing a symptom or condition associated with gout or hyperuricemia.

BACKGROUND

The background description includes information that may be useful in understanding the present invention. It is not an admission that any of the information provided herein is prior art or relevant to the presently claimed invention, or that any publication specifically or implicitly referenced is prior art.

Hyperuricemia is caused by the overproduction or underexcretion of uric acid, and is considered to be a causative factor of several diseases that significantly impair the quality of life. For example, hyperuricemia is considered the causative factor of gout—the most prevalent form of inflammatory arthritis, characterized by severe pain and tenderness in joints caused by urate crystal accumulation.

Uricosuric agents and xanthine oxidase inhibitors are often prescribed to lower uric acid levels and treat an underlying cause of gout. Xanthine oxidase inhibitors such as allopurinol or febuxostat can reduce the formation of uric acid, and uricosuric agents can inhibit the absorption of uric acid from the kidney back to the blood via the URAT1 transporter.

Benzbromarone is a uricosuric agent and could be an inhibitor of xanthine oxidase, and is known to be highly effective in lowering serum uric acid (sUA). It has been found that therapy using benzbromarone can lead to lowering of sUA even following a single dose and continue to be lowered following multiple doses, and that chronic therapy can bring sUA into target levels of <6 mg/dL. Unfortunately, like many other drugs, benzbromarone is associated with rare cases of hepatotoxicity and acute liver failure. The toxicity of the drug was believed by many to outweigh the benefits, and benzbromarone was reduced to limited use in the European market by its sponsor in 2003.

Several attempts have been made to formulate compounds and pharmaceuticals with high potency, and reduced toxicity, for example in U.S. 2013/0225673 (to Wempe et al.) describes uric acid transport inhibitors that can potentially be applied topically. Unfortunately and in part because the mechanism of damage/toxicity has not been clear, all or almost all prior attempts suffer from several disadvantages. For example, there is no evidence of the reproducibility and effectiveness of topical administration of such compounds.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

There have been many efforts to stabilize drugs and reduce production of unwanted metabolites. For example, US 2016/0031879 to Karra et al. teaches deuterated indolizine compounds to stabilize drugs for the treatment of multiple sclerosis and Alzheimer's disease. Karra, however, does not appear to teach application of this approach to modified benzbromarone compounds.

Others, for example in US 2015/031768 to Groves et al., have contemplated modifying some carbon containing compounds. However, the taught modifications were directed to labeling such compounds to generate imaging agents for PET applications, and not directed towards reducing toxicity.

Thus, there is still a need in the art for a highly potent gout/hyperuricemia drug with reduced toxicity.

SUMMARY OF THE INVENTION

Recent developments in hepatic clearance of benzbromarone has shown that significant portion of benzbromarone's biotransformation is mediated through CYP2C9, and benzbromarone itself is a potent CYP2C9 inhibitor. This complex interplay limited the identification of cause of liver toxicity both in vitro and in vivo, although the involvement of CYP2C9 is generally believed to be a cause of liver toxicity (particularly in poor CYP2C9 metabolizers).

Applicant has developed a series of compounds that show improved stability and reduction in the dependence on the CYP2C9 biotransformation pathway relative to benzbromazone, but that retain the activity of benzbromarone against URAT1 transporter.

The inventive subject matter provides compounds, compositions, and methods in which a novel compound represented by Formula 1, is capable of lowering serum acid (sUA) for the treatment of gout.

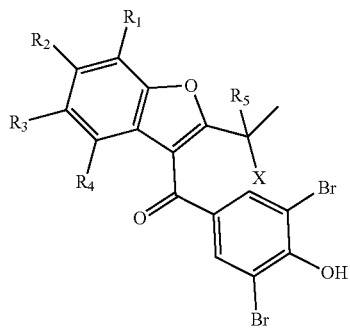

Formula 1

Applicant has found that compounds of Formula 1 wherein —X is —OH, —OR, —OC(O)R, —NH$_3$+, —NO$_2$, —SO$_2$R, —CN, —SO$_3$H, —CHO, —COOH, —COCl, —CONH$_2$, —F, —Cl, —Br or —I, where —R is a —H, —C$_1$-C$_{10}$ alkyl, or a —C$_1$-C$_{10}$ substituted alkyl; where —R$_1$, —R$_2$, —R$_3$, —R$_4$ and —R$_5$ are each independently selected from —H, -deuterium, —F, —Cl, —Br, —I, —CN, —C$_1$-C$_6$-alkyl, C$_6$-C$_{14}$-aryl, substituted —C$_6$-C$_{14}$-aryl, C$_1$-C$_{14}$-alkoxy, -hydroxyl, -carboxyl, —C$_1$-C$_6$-alkylsulfonyl, -trifluoromethyl, —C$_1$-C$_6$-alkanoyloxy, —C$_1$-C$_6$-alkylthio, —C$_1$-C$_6$-alkylsulfonyl, —C$_2$-C$_6$-alkoxycarbonyl, —C$_2$-C$_6$-alkanoylamino, —O—R$_6$, —S$_2$R$_6$, —SO$_2$—R$_6$, —NHSO$_2$R$_6$, and —NHCO$_2$R$_6$, where —R$_6$ is phenyl or naphthyl, and optionally substituted with one to three groups selected from —C$_1$-C$_6$-alkyl, —C$_6$-C$_{10}$-aryl, —C$_1$-C$_6$-alkoxy and halogen, and —C$_4$-C$_{20}$-hydroxyheteroaryl, and where the heteroatoms in —C$_4$-C$_{20}$-hydroxyheteroaryl are selected from nitrogen or oxygen; and where at least one of —R$_1$, —R$_2$, —R$_3$, —R$_4$ and —R$_5$ is -deuterium or a halogen (e.g., —F, —Cl, —Br, —I) when X is a halogen, —OH, or —OR, are useful for this purpose.

The chemically modified benzbromarone (BBR) compounds presented herein reduce CYP2C9 involvement in the biotransformation of one or more parent compound(s) and subject matter is shown below in Schemes 1 and 2. Building blocks (D) and (F) (Formula 5 and Formula 7, respectively) can be synthesized from (A) (Formula 2) with procedures from Scheme 1. Phenol (A) (Formula 2) reacts with formaldehyde with MgCl$_2$ to produce aldehyde (B) (Formula 3). Subsequent reaction of (B) (Formula 3) with choloracetone produces ketone (C) (Formula 4). Fluorination of (C) (Formula 4) produces di-fluoro compound (D) (Formula 5). Alternatively or additionally, reduction of (C) (Formula 4) gives alcohol (E) (Formula 6), which undergoes fluorination to produce mono-fluoro product (F) (Formula 7). It is contemplated that a compound of the inventive subject matter (I) (Formula 10) can be made from starting material (F) (Formula 7) or (D) (Formula 5) in three steps, as shown in Scheme 2. (F) (Formula 7) or (D) (Formula 5) can be treated with anisoyl chloride to form an intermediate product (G) (Formula 8), followed by demethylation by sodium ethanethiolate (NaSEt) to produce alcohol (H) (Formula 9), followed by bromination with Br$_2$ in acetic acid (e.g., at room temperature) to form a compound of the inventive subject matter (I) (Formula 10).

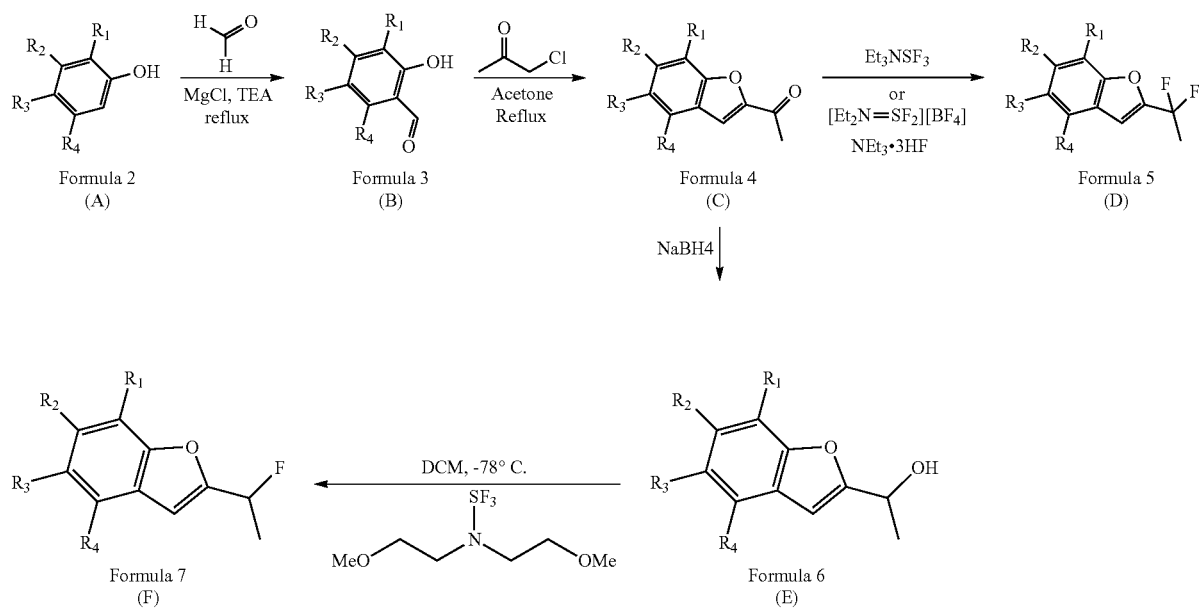

are presumed to be capable of reducing liver toxicity, while providing the hyperuricemia treating and URAT1 inhibiting benefits of BBR (in particular, for poor CYP2C9 metabolizers).

In some contemplated methods, genetic, gene expression, proteomic, or other (for example, metabolic and/or metabolite) tests can be administered to determine the presence of genotypes that affect the metabolism of a drug metabolized by CYP2C9. When, for example, a patient is determined to be a poor CYP2C9 metabolizer, a compound or composition of the inventive subject matter can be provided, alone or in combination with one or more other compositions, to reduce the likelihood of liver failure.

The person having ordinary skill in the art should be apprised of many ways to synthesize compounds of the inventive subject matter. For example, one contemplated general scheme for producing a compound of the inventive

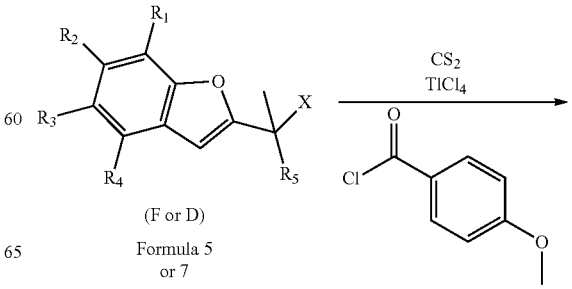

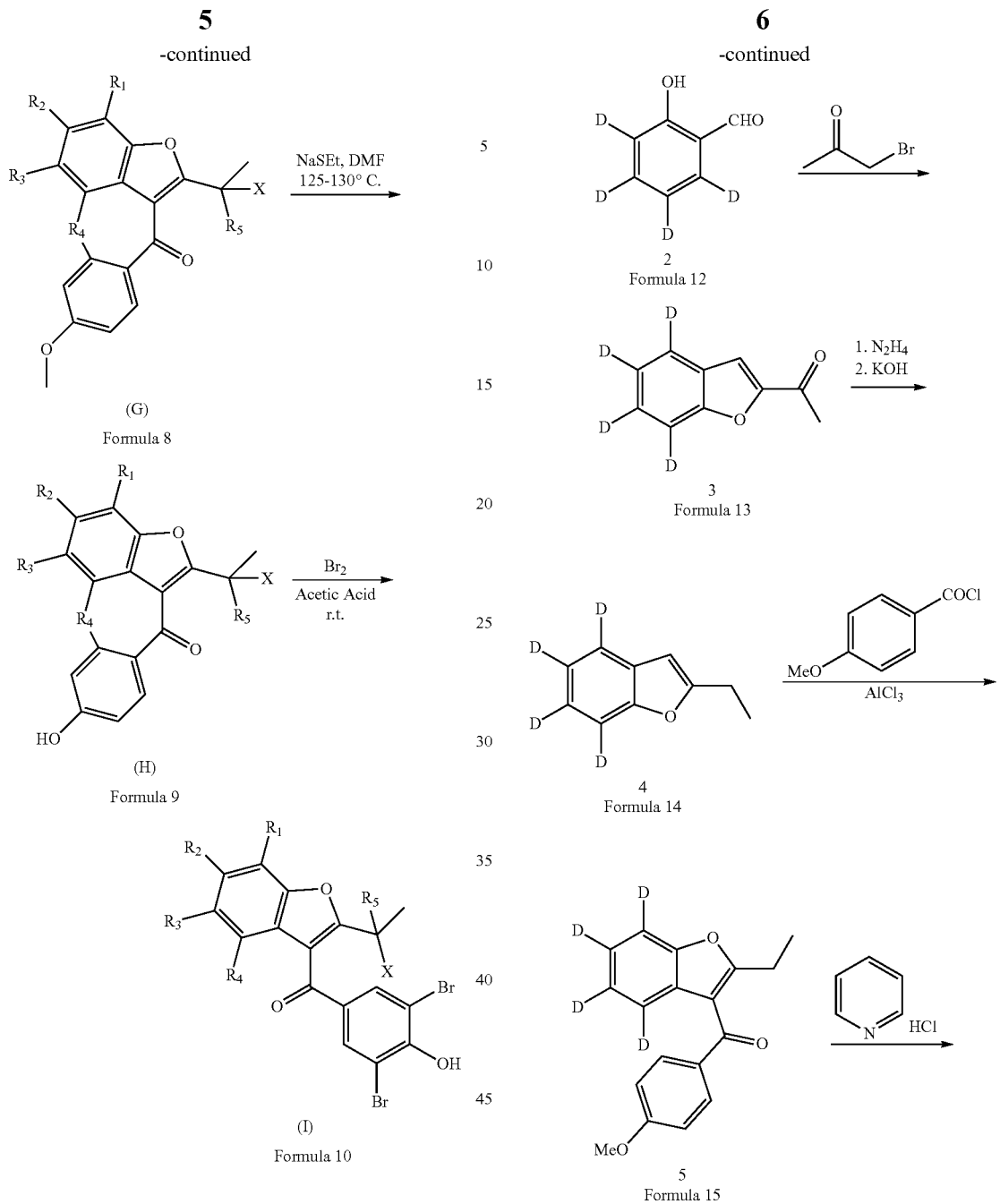
As another example, (2,6-dibromo-4-hydroxyphenyl)(2-(1-fluoroethy)benzofuran-3-yl-4,5,6,7-$D_4$)methanone (Formula 22) can be synthesized as shown in Scheme 3:
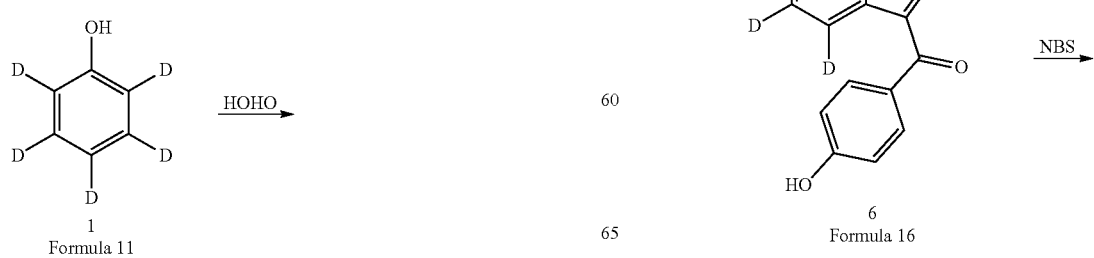

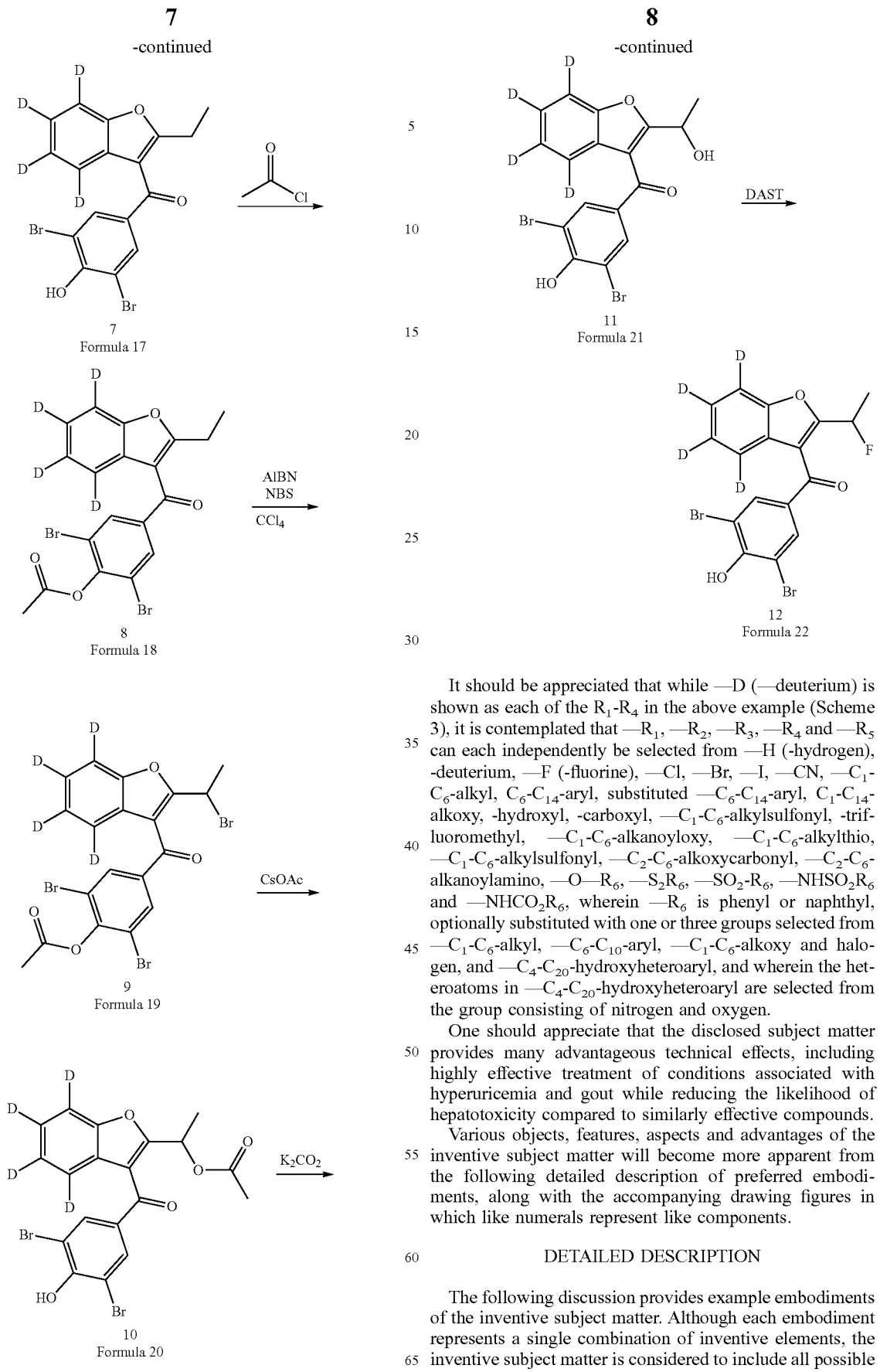

It should be appreciated that while —D (—deuterium) is shown as each of the $R_1$-$R_4$ in the above example (Scheme 3), it is contemplated that —$R_1$, —$R_2$, —$R_3$, —$R_4$ and —$R_5$ can each independently be selected from —H (-hydrogen), -deuterium, —F (-fluorine), —Cl, —Br, —I, —CN, —$C_1$-$C_6$-alkyl, $C_6$-$C_{14}$-aryl, substituted —$C_6$-$C_{14}$-aryl, $C_1$-$C_{14}$-alkoxy, -hydroxyl, -carboxyl, —$C_1$-$C_6$-alkylsulfonyl, -trifluoromethyl, —$C_1$-$C_6$-alkanoyloxy, —$C_1$-$C_6$-alkylthio, —$C_1$-$C_6$-alkylsulfonyl, —$C_2$-$C_6$-alkoxycarbonyl, —$C_2$-$C_6$-alkanoylamino, —O—$R_6$, —$S_2R_6$, —$SO_2$-$R_6$, —$NHSO_2R_6$ and —$NHCO_2R_6$, wherein —$R_6$ is phenyl or naphthyl, optionally substituted with one or three groups selected from —$C_1$-$C_6$-alkyl, —$C_6$-$C_{10}$-aryl, —$C_1$-$C_6$-alkoxy and halogen, and —$C_4$-$C_{20}$-hydroxyheteroaryl, and wherein the heteroatoms in —$C_4$-$C_{20}$-hydroxyheteroaryl are selected from the group consisting of nitrogen and oxygen.

One should appreciate that the disclosed subject matter provides many advantageous technical effects, including highly effective treatment of conditions associated with hyperuricemia and gout while reducing the likelihood of hepatotoxicity compared to similarly effective compounds.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The inventive subject matter provides compounds, compositions, and methods in which a novel compound represented by Formula 1 is provided:

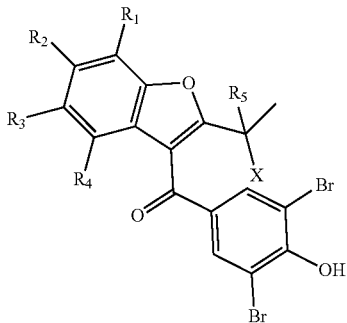

Formula 1

It should be appreciated that, as depicted in Formula 1, —X can be —OH, —OR, —OC(O)R, —NH$_3$+, —NO$_2$, —SO$_2$R, —CN, —SO$_3$H, —CHO, —COOH, —COCl, —CONH$_2$, —F, —Cl, —Br, or —I; —R can be a —H, —C$_1$-C$_{10}$ alkyl or a —C$_1$-C$_{10}$ substituted alkyl; —R$_1$, —R$_2$, —R$_3$, —R$_4$ and —R$_5$ can each independently be —H, -deuterium, —F, —Cl, —Br, —I, —CN, —C$_1$-C$_6$-alkyl, C$_6$-C$_{14}$-aryl, substituted —C$_6$-C$_{14}$-aryl, C$_1$-C$_{14}$-alkoxy, -hydroxyl, -carboxyl, —C$_1$-C$_6$-alkylsulfonyl, -trifluoromethyl, —C$_1$-C$_6$-alkanoyloxy, —C$_1$-C$_6$-alkylthio, —C$_1$-C$_6$-alkylsulfonyl, —C$_2$-C$_6$-alkoxycarbonyl, —C$_2$-C$_6$-alkanoylamino, —O—R$_6$, —S$_2$R$_6$, —SO$_2$— R$_6$, —NHSO$_2$R$_6$, or —NHCO$_2$R$_6$; —R$_6$ can be phenyl or naphthyl, and in some embodiments substituted with one to three groups selected from —C$_1$-C$_6$-alkyl, —C$_6$-C$_{10}$-aryl, —C$_1$-C$_6$-alkoxy, halogen, and —C$_4$-C$_{20}$-hydroxyheteroaryl, where the heteroatoms in —C$_4$-C$_{20}$-hydroxyheteroaryl can be nitrogen or oxygen.

In some embodiments, at least one of —R$_1$, —R$_2$, —R$_3$, —R$_4$ and —R$_5$ is -deuterium when X is a halogen, —OH, and/or a pharmaceutically acceptable pro-drug. In some contemplated embodiments, —X is —OH or —F, R$_3$ is a halogen (—F, —Cl, —Br or —I), and —R$_1$, —R$_2$, —R$_4$, and —R$_5$ are each independently selected from —H or deuterium. In some other contemplated embodiments, —R$_1$, —R$_2$, —R$_3$, and —R$_4$ are each deuterium, —X is —OH, and —R$_5$ is hydrogen. In some contemplated embodiments, —R$_1$, —R$_2$, —R$_3$, and —R$_4$ are each deuterium, —X is —F, and —R$_5$ is hydrogen. In some contemplated embodiments, —R$_1$, —R$_2$, and —R$_4$ are each deuterium, —X is OH, —R$_3$ is —F, and —R$_5$ is hydrogen. In some contemplated embodiments, —R$_1$, —R$_2$, —R$_3$, —R$_4$, and —R$_5$ are each independently selected from hydrogen and deuterium, and —X is —OH. In some contemplated embodiments, —R$_1$, —R$_2$, —R$_3$, and —R$_4$ are each independently selected from hydrogen and deuterium, —X is a —F or —OH, and —R$_5$ is hydrogen, —F, or deuterium. However, it is also contemplated that compounds of the inventive subject matter could include a halogen, for example fluorine at the 1' position, and comprise a hydrogen at each of the —R$_1$, —R$_2$, —R$_3$, —R$_4$ and —R$_5$ positions.

In some contemplated embodiments, X is —OH, —R$_1$, —R$_2$, —R$_3$, and —R$_4$ are each deuterium, and —R$_5$ is —H. As another example, in some contemplated embodiments, X is —F, —R$_1$, —R$_2$, —R$_3$, and —R$_4$ are each deuterium, and —R$_5$ is —H. As another example, in some contemplated embodiments, X and —R$_3$ are each —F, and —R$_1$, —R$_2$, —R$_4$, and —R$_5$ are each —H. As yet another example, in some contemplated embodiments, X is —OH, —R$_3$ is —F, and —R$_1$, —R$_2$, —R$_4$, and —R$_5$ are each —H.

It should be appreciated that in some embodiments, for example where a compound includes a —F in the —R$_3$ position, —R$_1$, —R$_2$, —R$_4$, and —R$_5$ could each be a —H. Viewed from a different perspective, it is contemplated that some compounds, for example compounds having —F in the —R$_3$ position, could lack deuterium.

In some contemplated embodiments, —X is —F (-fluorine). For example, some contemplated compounds include-deuterium at —R$_2$, —F at —X, —H at each of —R$_1$, —R$_3$, and —R$_4$, and —H at —R$_5$. In some contemplated compounds, —X is —F, each of —R$_2$ and —R$_4$ is -deuterium, and each of —R$_1$, —R$_3$, and —R$_5$ is a —H. In some other contemplated compounds, —X is —F, each of —R$_2$ and —R$_3$ is -deuterium, and each of —R$_1$, —R$_4$, and —R$_5$ is a —H. In yet other contemplated embodiments, —X is —F, each of —R$_1$, —R$_2$, —R$_3$ and —R$_4$, is -deuterium, and —R$_5$ is a —H. Compounds wherein —X is —F, each of —R$_1$, —R$_2$, —R$_3$ and —R$_4$ is -deuterium, and —R$_5$ is a —H are also contemplated.

In some contemplated embodiments, both the —X and —R$_5$ are fluorinated. For example, in some contemplated compounds, each of —X and —R$_5$ is —F, —R$_2$, is -deuterium, and each of —R$_1$, —R$_3$ and —R$_4$, is a —H. In some other contemplated embodiments, each of —X and —R$_5$ is —F, and each of —R$_1$, —R$_2$, —R$_3$ and —R$_4$ is -deuterium.

The inventive subject matter also provides compounds, compositions and methods in which novel compounds represented by Formula 23 and/or 24 are provided:

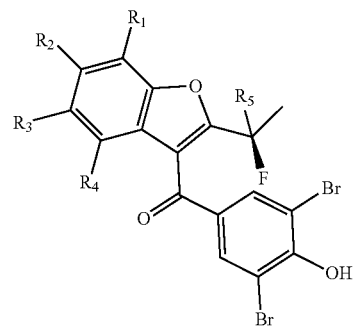

Formula 23

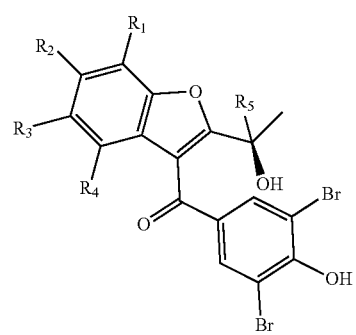

Formula 24

In such compounds —R$_1$, —R$_2$, —R$_3$, —R$_4$ and —R$_5$ are each independently selected from —H, -deuterium, —F, —Cl, —Br, —I, —CN, —C$_1$-C$_6$-alkyl, C$_6$-C$_{14}$-aryl, substituted —C$_6$-C$_{14}$-aryl, C$_1$-C$_{14}$-alkoxy, -hydroxyl, -carboxyl, —C$_1$-C$_6$-alkylsulfonyl, -trifluoromethyl, —C$_1$-C$_6$-alkanoyloxy, —C$_1$-C$_6$-alkylthio, —C$_1$-C$_6$-alkylsulfonyl, —C$_2$-C$_6$-alkoxycarbonyl, —C$_2$-C$_6$-alkanoylamino, —O—R$_6$, —S$_2$R$_6$, —SO$_2$—R$_6$, —NHSO$_2$R$_6$, and —NHCO$_2$R$_6$, where —R$_6$ is phenyl or naphthyl, and can be substituted with one to three groups selected from —C$_1$-C$_6$-alkyl, —C$_6$-C$_{10}$-aryl, —C$_1$-C$_6$-alkoxy and halogen, and —C$_4$-C$_{20}$-hydroxyheteroaryl, and where the heteroatoms in —C$_4$-C$_{20}$-hydroxyheteroaryl are nitrogen or oxygen.

The inventive subject matter also provides compounds, compositions and methods in which a novel compounds represented by Formula 25 and/or 26 are provided:

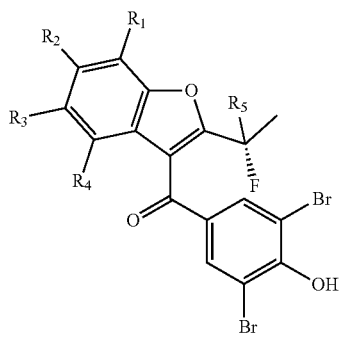

Formula 25

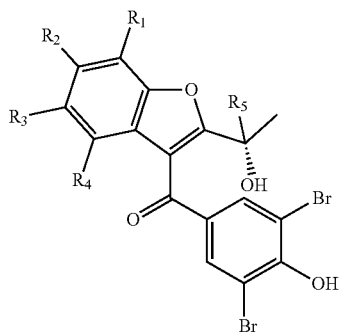

Formula 26

In such compounds —R$_1$, —R$_2$, —R$_3$, —R$_4$ and —R$_5$ can each be independently selected from —H, -deuterium, —F, —Cl, —Br, —I, —CN, —C$_1$-C$_6$-alkyl, C$_6$-C$_{14}$-aryl, substituted —C$_6$-C$_{14}$-aryl, C$_1$-C$_{14}$-alkoxy, -hydroxyl, -carboxyl, —C$_1$-C$_6$-alkylsulfonyl, -trifluoromethyl, —C$_1$-C$_6$-alkanoyloxy, —C$_1$-C$_6$-alkylthio, —C$_1$-C$_6$-alkylsulfonyl, —C$_2$-C$_6$-alkoxycarbonyl, —C$_2$-C$_6$-alkanoylamino, —O—R$_6$, —S$_2$R$_6$, —SO$_2$— R$_6$, —NHSO$_2$R$_6$, and —NHCO$_2$R$_6$, where —R$_6$ is phenyl or naphthyl, and optionally substituted with one or three groups selected from —C$_1$-C$_6$-alkyl, —C$_6$-C$_{10}$-aryl, —C$_1$-C$_6$-alkoxy and halogen, and —C$_4$-C$_{20}$-hydroxyheteroaryl, and wherein the heteroatoms in —C$_4$-C$_{20}$-hydroxyheteroaryl are selected from nitrogen or oxygen.

Viewed from another perspective, the inventive subject matter provides, among other compounds, the following (or salts, chelates, or pro-drugs thereof) compounds, formulations including one or more of the following compounds, and methods of treating a condition associated with hyperuricemia or gout that includes administering a formulation including a therapeutically effective amount of one or more of the following compounds:

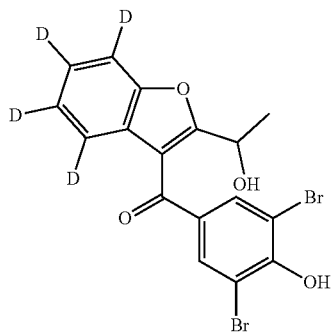

Formula 27

2,6-dibromo-4-[2-(1-hydroxyethyl)(4, 5,6,7-$^2$H$_4$)-1-benzofuran-3-carbonyl]phenol

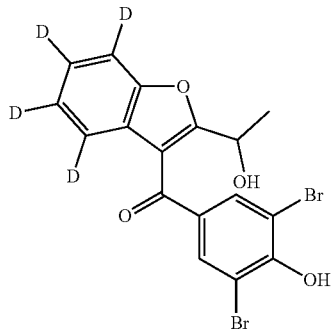

Formula 28

2,6-dibromo-4-[5-fluoro-2-(1-hydroxyethyl)(4, 6,7-$^2$H$_3$)-1-benzofuran-3-carbonyl]phenol

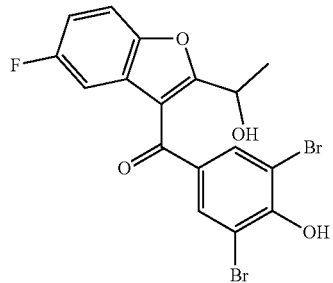

Formula 29

2,6-dibromo-4-[5-fluoro-2-(1-hydroxyethyl)-1-benzofuran-3-carbonyl]phenol

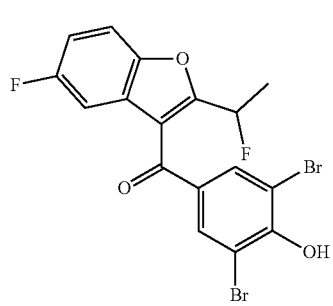

Formula 30

13

2,6-dibromo-4-[5-fluoro-2-(1-fluoroethyl)-1-benzo-
furan-3-carbonyl]phenol

14

2,6-dibromo-4-[2-(1-fluoroethyl)(4, 6-²H₂)-1-benzo-
furan-3-carbonyl]phenol

Formula 31

Formula 34

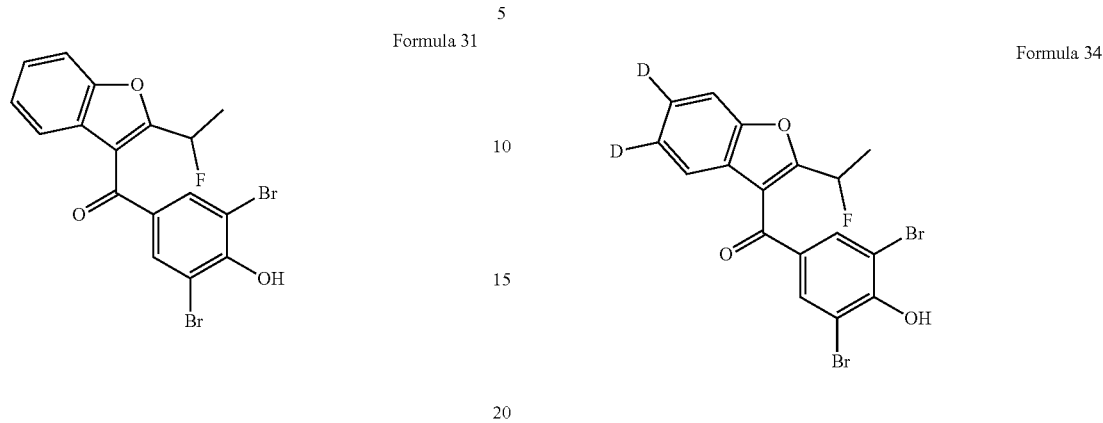

2,6-dibromo-4-[2-(1-fluoroethyl)-1-benzofuran-3-
carbonyl]phenol 2,6-dibromo-4-[2-(1-fluoroethyl)(5, 6-²H₂)-1-benzo-
furan-3-carbonyl]phenol Formula 32

Formula 35

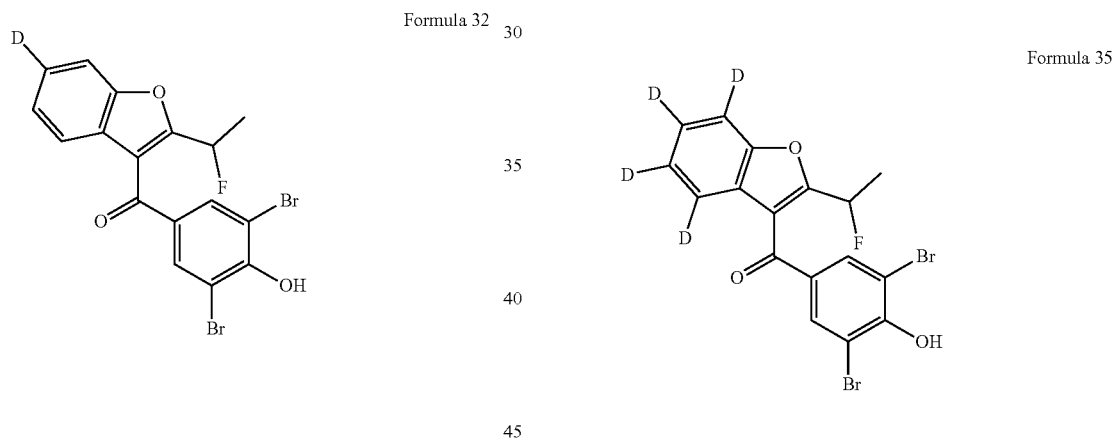

2,6-dibromo-4-[2-(1-fluoroethyl)(6-²H)-1-benzo-
furan-3-carbonyl]phenol 2,6-dibromo-4-[2-(1-fluoroethyl)(²H₄)-1-benzo-
furan-3-carbonyl]phenol Formula 33

Formula 36

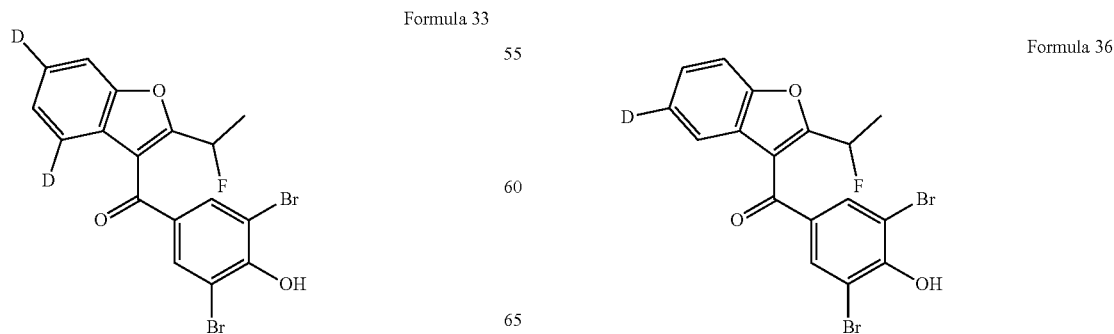

15

2,6-dibromo-4-[2-(1-fluoroethyl)(5-²H)-1-benzofuran-3-carbonyl]phenol

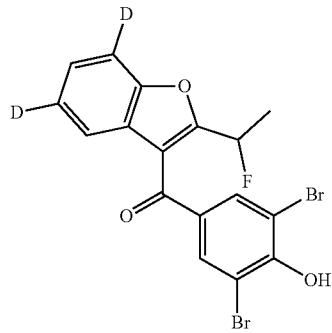

Formula 37

2,6-dibromo-4-[2-(1-fluoroethyl)(5,7-²H₂)-1-benzofuran-3-carbonyl]phenol

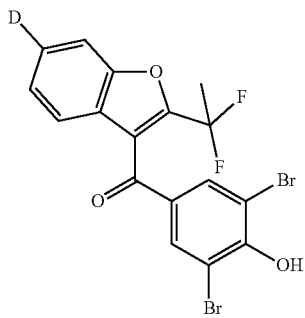

Formula 38

2,6-dibromo-4-[2-(1,1-difluoroethyl)(6-²H)-1-benzofuran-3-carbonyl]phenol

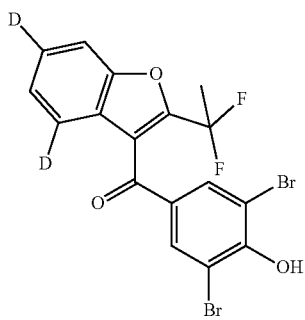

Formula 39

16

2,6-dibromo-4-[2-(1,1-difluoroethyl)(4,6-²H₂)-1-benzofuran-3-carbonyl]phenol

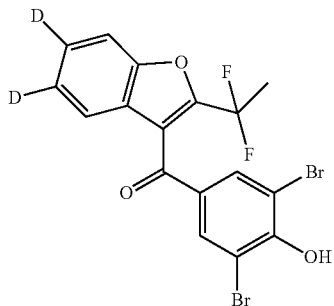

Formula 40

2,6-dibromo-4-[2-(1,1-difluoroethyl)(5,6-²H₂)-1-benzofuran-3-carbonyl]phenol

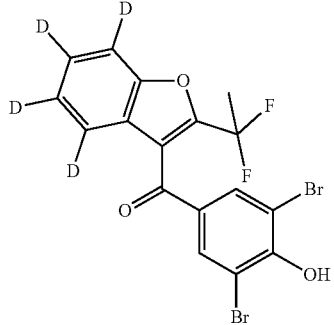

Formula 41

2,6-dibromo-4-[2-(1,1-difluoroethyl)(²H₄)-1-benzofuran-3-carbonyl]phenol

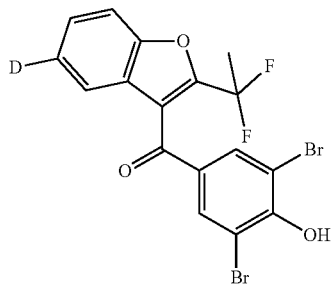

Formula 42

17

2,6-dibromo-4-[2-(1,1-difluoroethyl)(5-²H)-1-benzo-
furan-3-carbonyl]phenol

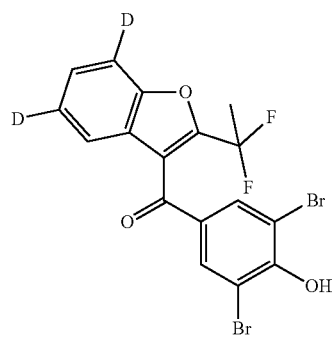

Formula 43

2,6-dibromo-4-[2-(1,1-difluoroethyl)(5,7-²H₂)-1-
benzofuran-3-carbonyl]phenol

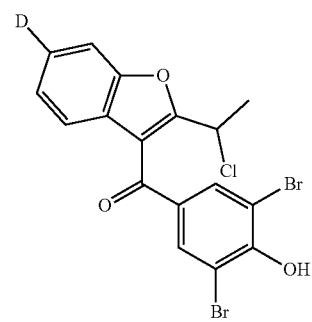

Formula 44

2,6-dibromo-4-[2-(1-chloroethyl)(6-²H)-1-benzo-
furan-3-carbonyl]phenol

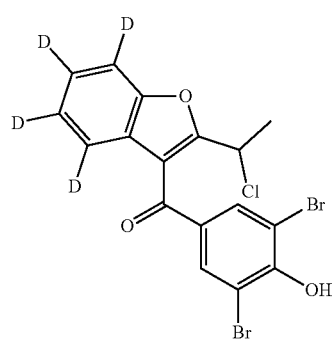

Formula 45

18

2,6-dibromo-4-[2-(1-chloroethyl)(2H₄)-1-benzo-
furan-3-carbonyl]phenol

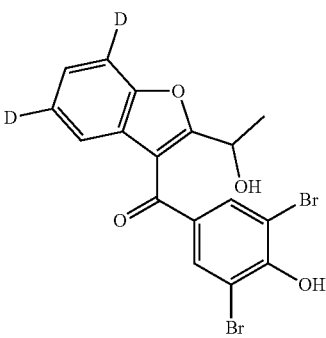

Formula 46

2,6-dibromo-4-[2-(1-hydroxyethyl)(5,6-²H₂)-1-ben-
zofuran-3-carbonyl]phenol

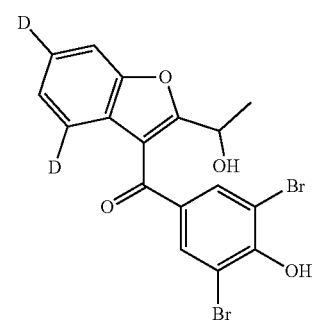

Formula 47

2,6-dibromo-4-[2-(1-hydroxyethyl)(4,6-²H₂)-1-ben-
zofuran-3-carbonyl]phenol

While the compounds of the inventive subject matter are thought to be useful for treating hyperuricemia or gout, treating conditions associated with hyperuricemia or gout, inhibiting one or more kidney transporters responsible for uric acid reabsorption in renal tubules, treating a condition, disorder or disease mediated by at least one kidney transporter responsible for uric acid reabsorption in renal tubules, and lowering serum uric acid through inhibition of purine catabolism, it should be appreciated that compounds of the inventive subject matter could be used in any commercially suitable manner now known or later discovered. It should therefore also be appreciated that compositions of the inventive subject matter could be used to treat or prevent any suitable condition, whether now known or later discovered.

The inventive subject matter also provides compounds, compositions and methods in which a composition for the treatment of a condition associated with hyperuricemia or gout is provided. The composition can include a pharmaceutically acceptable carrier, and a compound of Formula 1 or a pharmaceutically acceptable salt thereof:

Formula 1

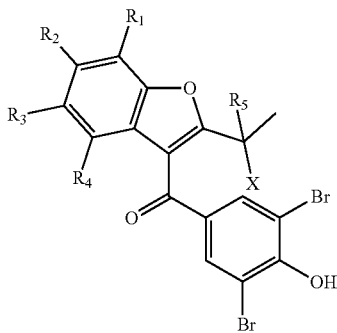

In such a compound and/or formulation —X can be —OH, —OR, —OC(O)R, —NH$_3$+, —NO$_2$, —SO$_2$R, —CN, —SO$_3$H, —CHO, —COOH, —COCl, —CONH$_2$, —F, —Cl, —Br, or —I, where —R can be a —H, —C$_1$-C$_{10}$ alkyl or a —C$_1$-C$_{10}$ substituted alkyl; where —R$_2$ can be -deuterium or —H; and where —R$_1$, —R$_3$, —R$_4$ and —R$_5$ are each independently selected from —H, -deuterium, —F, —Cl, —Br, —I, —CN, —C$_1$-C$_6$-alkyl, C$_6$-C$_{14}$-aryl, substituted —C$_6$-C$_{14}$-aryl, C$_1$-C$_{14}$-alkoxy, -hydroxyl, -carboxyl, —C$_1$-C$_6$-alkylsulfonyl, -trifluoromethyl, —C$_1$-C$_6$-alkanoyloxy, —C$_1$-C$_6$-alkylthio, —C$_1$-C$_6$-alkylsulfonyl, —C$_2$-C$_6$-alkoxycarbonyl, —C$_2$-C$_6$-alkanoylamino, —O—R$_6$, —S$_2$R$_6$, —SO$_2$—R$_6$, —NHSO$_2$R$_6$, and —NHCO$_2$R$_6$, where —R$_6$ can be phenyl or naphthyl, and optionally substituted with one to three groups selected from —C$_1$-C$_6$-alkyl, —C$_6$-C$_{10}$-aryl, —C$_1$-C$_6$-alkoxy and halogen, and —C$_4$-C$_{20}$-hydroxyheteroaryl, and where the heteroatoms in —C$_4$-C$_{20}$-hydroxyheteroaryl are nitrogen or oxygen; and where the compound of Formula 1 is present in a therapeutically effective amount to treat a condition associated with hyperuricemia.

In some embodiments, —R$_1$, —R$_2$, —R$_3$, —R$_4$ and —R$_5$ is -deuterium when X is a halogen, —OH, or one or more pharmaceutically acceptable pro-drugs. In some contemplated embodiments, —X can be —OH or —F, R$_3$ can be a halogen (e.g. —F, —Cl, —Br or —I), and —R$_1$, —R$_2$, —R$_4$, and —R$_5$ are each independently selected from —H or deuterium. In some other contemplated embodiments, —R$_1$, —R$_2$, —R$_3$, and —R$_4$ are each deuterium, —X is —OH, and —R$_5$ is hydrogen. In some contemplated embodiments, —R$_1$, —R$_2$, —R$_3$, and —R$_4$ are each deuterium, —X is —F, and —R$_5$ is hydrogen. In some contemplated embodiments, —R$_1$, —R$_2$, and —R$_4$ are each deuterium, —X is OH, —R$_3$ is —F, and —R$_5$ is hydrogen. In some contemplated embodiments, —R$_1$, —R$_2$, —R$_3$, —R$_4$. and —R$_5$ are each independently selected from hydrogen and deuterium, and —X is —OH. In some contemplated embodiments, —R$_1$, —R$_2$, —R$_3$, and —R$_4$ are each independently selected from hydrogen and deuterium, —X is a —F or —OH, and —R$_5$ is hydrogen, —F, or deuterium. However, it is also contemplated that compounds of the inventive subject matter could include a halogen, for example fluorine at the 1' position, and comprise a hydrogen at each of the —R$_1$, —R$_2$, —R$_3$, —R$_4$ and —R$_5$ positions.

For example, in some contemplated embodiments, X is —OH, —R$_1$, —R$_2$, —R$_3$, and —R$_4$ are each deuterium, and —R$_5$ is —H. As another example, in some contemplated embodiments, X is —F, —R$_1$, —R$_2$, —R$_3$, and —R$_4$ are each deuterium, and —R$_5$ is —H. In another example, in some contemplated embodiments, X and —R$_3$ are each —F, and —R$_1$, —R$_2$, —R$_4$, and —R$_5$ are each —H. As yet another example, in some contemplated embodiments, X is —OH, —R$_3$ is —F, and —R$_1$, —R$_2$, —R$_4$, and —R$_5$ are each —H.

In some contemplated embodiments, —X is —F (fluorine). For example, some contemplated compounds include-deuterium at —R$_2$, —F at —X, —H at each of —R$_1$, —R$_3$, and —R$_4$, and —H at —R$_5$. In some contemplated compounds, —X is —F, each of —R$_2$ and —R$_4$ is -deuterium, and each of —R$_1$, —R$_3$, and —R$_5$ is a —H. In some other contemplated compounds, —X is —F, each of —R$_2$ and —R$_3$ is -deuterium, and each of —R$_1$, —R$_4$, and —R$_5$ is a —H. In yet other contemplated embodiments, —X is —F, each of —R$_1$, —R$_2$, —R$_3$ and —R$_4$, is -deuterium, and —R$_5$ is a —H. Compounds wherein —X is —F, each of —R$_1$, —R$_2$, —R$_3$ and —R$_4$ is -deuterium, and —R$_5$ is a —H are also contemplated.

In some contemplated embodiments, both the —X and —R$_5$ are fluorinated. For example, in some contemplated compounds, each of —X and —R$_5$ is —F, —R$_2$, is -deuterium, and each of —R$_1$, —R$_3$ and —R$_4$, is a —H. In some other contemplated embodiments, each of —X and —R$_5$ is —F, and each of —R$_1$, —R$_2$, —R$_3$ and —R$_4$ is -deuterium.

In some contemplated embodiments, —X is —Cl (chlorine). For example, some contemplated compounds include-deuterium at —R$_2$, —Cl at —X, —H at each of —R$_1$, —R$_3$, and —R$_4$, and —H at —R$_5$. In some contemplated compounds, —X is —Cl, each of —R$_2$ and —R$_4$ is -deuterium, and each of —R$_1$, —R$_3$, and —R$_5$ is a —H. In some other contemplated compounds, —X is —Cl, each of —R$_2$ and —R$_3$ is -deuterium, and each of —R$_1$, —R$_4$, and —R$_5$ is a —H. In yet other contemplated embodiments, —X is —Cl, each of —R$_1$, —R$_2$, —R$_3$ and —R$_4$, is -deuterium, and —R$_5$ is a —H. Compounds wherein —X is —Cl, each of —R$_1$, —R$_2$, —R$_3$ and —R$_4$ is -deuterium, and —R$_5$ is a —H are also contemplated.

In some contemplated embodiments, both the —X and —R$_5$ are chlorinated. For example, in some contemplated compounds, each of —X and —R$_5$ is —Cl, —R$_2$, is -deuterium, and each of —R$_1$, —R$_3$ and —R$_4$, is a —H. In some other contemplated embodiments, each of —X and —R$_5$ is —Cl, and each of —R$_1$, —R$_2$, —R$_3$ and —R$_4$ is -deuterium.

In some contemplated embodiments, both the —X and —R$_5$ are halogenated. For example, in some contemplated compounds, —X is —Cl, —Br, —I, or —F, —R$_5$ is —Cl, —Br, —I, or —F, —R$_2$, is -deuterium, and each of —R$_1$, —R$_3$ and —R$_4$, is a —H. In some other contemplated embodiments, —X is —Cl, —Br, —I, or —F, —R$_5$ is —Cl, —Br, —I, or —F, and each of —R$_1$, —R$_2$, —R$_3$ and —R$_4$ is -deuterium.

In some contemplated embodiments, the condition associated with hyperuricemia to be treated is at least one of gout, hypertension, hypothyroidism, renal insufficiency, obesity, and diabetes. In some contemplated embodiments, the compositions can be used to treat a condition other than hyperuricemia or one associated with hyperuricemia.

The compositions according to the inventive subject matter may be administered using various routes, including orally, parenterally, by inhalation, topically, via a mucus membrane (e.g. rectally, nasally, vaginally, etc.), and/or via an implanted reservoir, wherein the term "parenteral" as used herein includes subcutaneous, intravenous, intramuscular, intraarticular, intrasynovial, intrathecal, intrahepatic, intralesional, and intracranial administration (typically injection or infusion). Preferably, the compositions are administered orally, intraperitoneally, or intravenously.

The pharmaceutically acceptable compositions of this invention may be orally administered in any orally acceptable dosage form including, but not limited to, capsules, tablets, troches, elixirs, suspensions, syrups, wafers, chewing gums, suspensions, and/or solutions. The term "therapeutically effective amount" refers to the amount of the compound or pharmaceutical composition that will elicit a biological or medical response of a tissue, system, animal or human that is being sought by the researcher, veterinarian, medical doctor or other clinician, e.g., reduction of sUA, reduction of occurrence or flare, pain, tophi, and reduction of morbidity.

With respect to the amount of contemplated compounds in the composition, it should be recognized that the particular quantity will typically depend on the specific formulation, active ingredient, and desired purpose. Therefore, it should be recognized that the amount of contemplated compounds will vary significantly. However, it is generally preferred that the compounds are present in a minimum amount effective to deliver a therapeutic effect or to be visualized in vitro or in vivo.

A dose of the composition according to the inventive subject matter may be selected appropriately depending on, among other things, one or more of the age, sex or weight of the person to be treated, the symptoms or severity of the condition, the route and frequency of administration, and the particular compound employed. Typically, the dose is normally from 0.01 to 500 mg/kg of body weight per day, more preferably from 0.1 to 100 mg, or from 0.1 to 50 mg/kg/day. In some contemplated embodiments, the composition is administered as a single dose. In some contemplated embodiments, the composition is administered in multiple doses. The administration of the suitable dose can be spread out over the course of a day, and can be administered, for example, 1-10 times per day. 1-5 times per day, 1-4 times per day, or 2-4 times per day. Viewed from another perspective, the dose of the composition administered to a person to be treated can be between 10-250 mg/day, between 10-100 mg/day, between 20-75 mg/day, 50-250 mg/day, 100-200 mg/day or any other suitable amount.

With respect to a dosage unit, it is generally contemplated that compounds are administered at a dosage effective to achieve a desired therapeutic effect or at a dosage effective to provide visualization in vitro or in vivo.

Depending on the particular use and structure, it is contemplated that the compounds according to the inventive subject matter are present in the composition in an amount between 1 microgram to 1000 milligram, more typically between 10 microgram to 500 milligram, and most typically between 10 mg to 250 mg per single dosage unit. Thus, concentrations of contemplated compounds in vivo or in vitro may be between 0.1 nM and 100 microM, more typically between 1 nM and 50 microM, and most typically between 10 nM and 10 microM.

The inventive subject matter also provides compounds, compositions and methods for treating a condition associated with hyperuricemia, diabetes or gout. Contemplated methods can include administering an effective amount of a composition comprising a pharmaceutically acceptable carrier and a compound of Formula 1, or a pharmaceutically acceptable salt thereof:

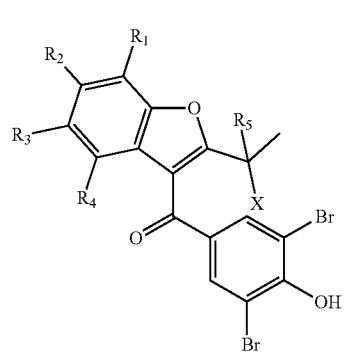

Formula 1

In such a compound —X can be —OH, —OR, —OC(O) R, —$NH_3+$, —$NO_2$, —$SO_2R$, —CN, —$SO_3H$, —CHO, —COOH, —COCl, —$CONH_2$, —F, —Cl, —Br, or —I, where —R can be —H, —$C_1$-$C_{10}$ alkyl, or a —$C_1$-$C_{10}$ substituted alkyl; where —$R_2$ is -deuterium or —H; and where —$R_1$, —$R_3$, —$R_4$ and —$R_5$ are each independently selected from —H, -deuterium, —F, —Cl, —Br, —I, —CN, —$C_1$-$C_6$-alkyl, $C_6$-$C_{14}$-aryl, substituted —$C_6$-$C_{14}$-aryl, $C_1$-$C_{14}$-alkoxy, -hydroxyl, -carboxyl, —$C_1$-$C_6$-alkylsulfonyl, -trifluoromethyl, —$C_1$-$C_6$-alkanoyloxy, —$C_1$-$C_6$-alkylthio, —$C_1$-$C_6$-alkylsulfonyl, —$C_2$-$C_6$-alkoxycarbonyl, —$C_2$-$C_6$-alkanoylamino, —O—$R_6$, —$S_2R_6$, —$SO_2$—$R_6$, —$NHSO_2R_6$, and —$NHCO_2R_6$, where —$R_6$ is phenyl or naphthyl, and optionally substituted with one to three groups selected from —$C_1$-$C_6$-alkyl, —$C_6$-$C_{10}$-aryl, —$C_1$-$C_6$-alkoxy and halogen, and —$C_4$-$C_{20}$-hydroxyheteroaryl, and where the heteroatoms in —$C_4$-$C_{20}$-hydroxyheteroaryl are nitrogen or oxygen.

In some contemplated embodiments, —X is a halogen or —OH. For example, some contemplated compounds include -deuterium or —H at —$R_2$, —F, —Cl, —Br, —I or —OH at —X, —H at each of —$R_1$, —$R_3$, and —$R_4$, and —$R_5$. In some contemplated compounds, —X is —F, —Cl, —Br, —I or —OH, each of —$R_2$ and —$R_4$ is -deuterium or —H, and each of —$R_1$, —$R_3$, and —$R_5$ is a —H. In some other contemplated compounds, —X is —F, —Cl, —Br, —I or —OH, each of —$R_2$ and —$R_3$ is -deuterium or —H, and each of —$R_1$, —$R_4$, and —$R_5$ is a —H. In yet other contemplated embodiments, —X is —F, —Cl, —Br, —I or —OH, each of —$R_1$, —$R_2$, —$R_3$ and —$R_4$, is -deuterium or —H, and —$R_5$ is a —H. In some contemplated compounds, for example, wherein —X is —F, —Cl, —Br, —I or —OH, each of —$R_1$, —$R_2$, —$R_3$ and —$R_4$ is -deuterium or —H, and —$R_5$ is a —H.

In some contemplated embodiments, —X is a halogen or —OH. For example, some contemplated compounds include -deuterium at —$R_2$, —F, —Cl, —Br, —I or —OH at —X, —H at each of —$R_1$, —$R_3$, and —$R_4$, and —$R_5$. In some contemplated compounds, —X is —F, —Cl, —Br, —I or —OH, each of —$R_2$ and —$R_4$ is -deuterium, and each of —$R_1$, —$R_3$, and —$R_5$ is a —H. In some other contemplated compounds, —X is —F, —Cl, —Br, —I or —OH, each of —$R_2$ and —$R_3$ is -deuterium, and each of —$R_1$, —$R_4$, and —$R_5$ is a —H. In yet other contemplated embodiments, —X is —F, —Cl, —Br, —I or —OH, each of —$R_1$, —$R_2$, —$R_3$ and —$R_4$, is -deuterium, and —$R_5$ is a —H. In some contemplated compounds, for example, wherein —X is —F, —Cl, —Br, —I or —OH, each of —$R_1$, —$R_2$, —$R_3$ and —$R_4$ is -deuterium, and —$R_5$ is a —H. In some contemplated compounds, —X is —F, —Cl, —Br, —I or —OH, —R$_3$ is —F, —Cl, —Br, —I or —OH, and —R$_1$, —R$_2$, —R$_4$ and —R$_5$ are —H.

In some contemplated embodiments, both the —X and —R$_5$ are halogenated. For example, in some contemplated compounds, each of —X and —R$_5$ is selected from —F, —Cl, —Br or —I, —R$_2$, is -deuterium, and each of —R$_1$, —R$_3$ and —R$_4$, is a —H. In some other contemplated embodiments, each of —X and —R$_5$ is each selected from —F, —Cl, —Br or —I, and each of —R$_1$, —R$_2$, —R$_3$ and —R$_4$ is -deuterium.

The inventive subject matter also provides compounds, compositions and methods for treating a condition associated with hyperuricemia or gout including combination treatments with, for example, one or more xanthine oxidase inhibitors such as allopurinol, oxypurinol, febuxostat, topiroxostat, inositols and a compound of Formula 1. Contemplated compounds, compositions and methods can include administering an effective amount of a composition comprising a xanthine oxidase inhibitor, and a pharmaceutically acceptable carrier and a compound of Formula 1, or a pharmaceutically acceptable salt thereof:

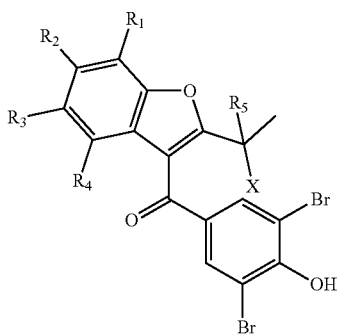

Formula 1

In such a compound —X can be —OH, —OR, —OC(O)R, —NH$_3$+, —NO$_2$, —SO$_2$R, —CN, —SO$_3$H, —CHO, —COOH, —COCl, —CONH$_2$, —F, —Cl, —Br, or —I, where —R can be —H, —C$_1$-C$_{10}$ alkyl, or a —C$_1$-C$_{10}$ substituted alkyl; where —R$_2$ is -deuterium or —H; and where —R$_1$, —R$_3$, —R$_4$ and —R$_5$ are each independently selected from —H, -deuterium, —F, —Cl, —Br, —I, —CN, —C$_1$-C$_6$-alkyl, C$_6$-C$_{14}$-aryl, substituted —C$_6$-C$_{14}$-aryl, C$_1$-C$_{14}$-alkoxy, -hydroxyl, -carboxyl, —C$_1$-C$_6$-alkylsulfonyl, -trifluoromethyl, —C$_1$-C$_6$-alkanoyloxy, —C$_1$-C$_6$-alkylthio, —C$_1$-C$_6$-alkylsulfonyl, —C$_2$-C$_6$-alkoxycarbonyl, —C$_2$-C$_6$-alkanoylamino, —O—R$_6$, —S$_2$R$_6$, —SO$_2$—R$_6$, —NHSO$_2$R$_6$, and —NHCO$_2$R$_6$, where —R$_6$ is phenyl or naphthyl, and optionally substituted with one to three groups selected from —C$_1$-C$_6$-alkyl, —C$_6$-C$_{10}$-aryl, —C$_1$-C$_6$-alkoxy and halogen, and —C$_4$-C$_{20}$-hydroxyheteroaryl, and where the heteroatoms in —C$_4$-C$_{20}$-hydroxyheteroaryl are nitrogen or oxygen.

In some contemplated embodiments, —X is a halogen or —OH. For example, some contemplated compounds include -deuterium or —H at —R$_2$, —F, —Cl, —Br, —I or —OH at —X, —H at each of —R$_1$, —R$_3$, and —R$_4$, and —R$_5$. In some contemplated compounds, —X is —F, —Cl, —Br, —I or —OH, each of —R$_2$ and —R$_4$ is -deuterium or —H, and each of —R$_1$, —R$_3$, and —R$_5$ is a —H. In some other contemplated compounds, —X is —F, —Cl, —Br, —I or —OH, each of —R$_2$ and —R$_3$ is -deuterium or —H, and each of —R$_1$, —R$_4$, and —R$_5$ is a —H. In yet other contemplated embodiments, —X is —F, —Cl, —Br, —I or —OH, each of —R$_1$, —R$_2$, —R$_3$ and —R$_4$, is -deuterium or —H, and —R$_5$ is a —H. In some contemplated embodiments, —X is a halogen or —OH. For example, some contemplated compounds include -deuterium at —R$_2$, —F, —Cl, —Br, —I or —OH at —X, —H at each of —R$_1$, —R$_3$, and —R$_4$, and —R$_5$. In some contemplated compounds, —X is —F, —Cl, —Br, —I or —OH, each of —R$_2$ and —R$_4$ is -deuterium, and each of —R$_1$, —R$_3$, and —R$_5$ is a —H. In some other contemplated compounds, —X is —F, —Cl, —Br, —I or —OH, each of —R$_2$ and —R$_3$ is -deuterium, and each of —R$_1$, —R$_4$, and —R$_5$ is a —H. In yet other contemplated embodiments, —X is —F, —Cl, —Br, —I or —OH, each of —R$_1$, —R$_2$, —R$_3$ and —R$_4$, is -deuterium, and —R$_5$ is a —H. In some contemplated compounds, for example, wherein —X is —F, —Cl, —Br, —I or —OH, each of —R$_1$, —R$_2$, —R$_3$ and —R$_4$ is -deuterium, and —R$_5$ is a —H. In some contemplated compounds, —X is —F, —Cl, —Br, —I or —OH, —R$_3$ is —F, —Cl, —Br, —I or —OH, and —R$_1$, —R$_2$, —R$_4$ and —R$_5$ are —H.

In some contemplated embodiments, both the —X and —R$_5$ are halogenated. For example, in some contemplated compounds, each of —X and —R$_5$ is selected from —F, —Cl, —Br or —I, —R$_2$, is -deuterium, and each of —R$_1$, —R$_3$ and —R$_4$, is a —H. In some other contemplated embodiments, each of —X and —R$_5$ is each selected from —F, —Cl, —Br or —I, and each of —R$_1$, —R$_2$, —R$_3$ and —R$_4$ is -deuterium.

In some contemplated embodiments, the condition to be treated is at least one of gout, hypertension and diabetes.

The term "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH$_2$)$_n$—COOH where n is 0-4, and the like.

Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred. Lists of suitable salts are found in at page 1418 of Remington's Pharmaceutical Sciences, 17th ed., Mack Publishing Company, Easton, Pa., 1985.

The term "solvate" refers to the compound formed by the interaction of a solvent and a compound. Suitable solvates are pharmaceutically acceptable solvates, such as hydrates, including monohydrates and hemi-hydrates.

The present invention provides compounds, as well as compositions of matter that are formulations of one or more active drugs and a pharmaceutically-acceptable carrier. In this regard, the invention provides a composition for administration to a mammalian subject, which may include one or more of the compounds presented herein, or its pharmaceutically acceptable salts, solvates, esters, chelates or prodrugs thereof.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

The term "pharmaceutically acceptable" refers to the fact that the carrier, diluent or excipient must be compatible with the other ingredients of the formulation and not deleterious to the recipient thereof.

The terms "administration of a compound" or "administering a compound" or "administering a composition" refer to the act of providing a compound of the invention or pharmaceutical composition to the subject in need of treatment. Where two or more compounds are administered, co-administration is typically preferred with the co-administration being either via a combination formulation, or via parallel or subsequent administration of the two compounds. Most typically sequential co-administration will be performed such that the first compound is present in the patient's body in measurable quantities when the second compound is administered.

Salts derived from appropriate bases include alkali metal (e.g., sodium and potassium), alkaline earth metal (e.g., magnesium, calcium), ammonium and N+(C1-4 alkyl)$_4$ salts. This invention also envisions the quaternization of any basic nitrogen-containing groups of the compounds disclosed herein. Water or oil-soluble or dispersible products may be obtained by such quaternization.

Any asymmetric atom of the compounds of the inventive subject matter can be present in racemic or enantiomerically enriched, for example the (R) or (S) configuration. Accordingly, as used herein a compound of the inventive subject matter can be in the form of one of the possible isomers, rotamers, or mixtures thereof, as substantially pure optical isomers, racemates or mixtures thereof. In some embodiments a formulation of the inventive concept can include a racemic mixture of enantiomers of one or more compounds of the inventive concept. In other embodiments a formulation of the inventive concept can include a majority (i.e. greater than about 50%) of a selected entantiomer of a compound of the inventive concept. In still other embodiments a formulation of the inventive concept can include only a single enantiomer of a compound of the inventive concept. Such enantiomer-enriched or single enantiomer formulations can provide effective treatment of conditions described herein, in some instances at reduced dosages and/or with fewer side effects relative to treatment with a formulation that includes a racemic mixture.

As used herein, the term "halo" or "halogen" refers to fluorine, chlorine, bromine or iodine.

The term "alkyl" herein alone or as part of another group refers to a monovalent alkane (hydrocarbon) derived radical containing from 1 to 12 carbon atoms unless otherwise defined. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, dimethylpentyl, octyl, 2,2,4-trimethylpentyl, nonyl, decyl, undecyl, dodecyl, and the like.

Exemplary substituents for radicals designated as "optionally substituted" include one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). In some embodiments of the present invention, alkyl groups are substituted with, for example, amino, or heterocycloalkyl, such as morpholine, piperazine, piperidine, azetidine, hydroxyl, methoxy, or a heteroaryl group, such as pyrrolidine.

The term "cycloalkyl" herein alone or as part of another group refers to fully saturated and partially unsaturated hydrocarbon rings of 3 to 9, preferably 3 to 7 carbon atoms. The examples include cyclopropyl, cyclobutyl, cyclopentyl and cyclohexyl, and like. Further, a cycloalkyl may be substituted. For example, a substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —$CO_2H$, —C(=O)H, $CO_2$-alkyl, —C(=O)alkyl, keto, =N—OH, =N—O-alkyl, aryl, heteroaryl, heterocyclo, —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" are independently selected from hydrogen, alkyl, substituted alkyl, and cycloalkyl, or R' and R" together form a heterocyclo or heteroaryl ring.

The term 'alkenyl" herein alone or as part of another group refers to a hydrocarbon radical straight, branched or cyclic containing from 2 to 12 carbon atoms and at least one carbon to carbon double bond. Examples of such groups include the vinyl, allyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, and like. Alkenyl groups may also be substituted at any available point of attachment. Exemplary substituents for alkenyl groups include those listed above for alkyl groups, and especially include C3 to C7 cycloalkyl groups such as cyclopropyl, cyclopentyl and cyclohexyl, which may be further substituted with, for example, amino, oxo, hydroxyl, etc.

The term "alkynyl" refers to straight or branched chain alkyne groups, which have one or more unsaturated carbon-carbon bonds, at least one of which is a triple bond. Alkynyl groups include C2-C8 alkynyl, C2-C6 alkynyl and C2-C4 alkynyl groups, which have from 2 to 8, 2 to 6 or 2 to 4 carbon atoms, respectively. Illustrative of the alkynyl group include ethenyl, propenyl, isopropenyl, butenyl, isobutenyl, pentenyl, and hexenyl. Alkynyl groups may also be substituted at any available point of attachment. Exemplary substituents for alkynyl groups include those listed above for alkyl groups such as amino, alkylamino, etc. The numbers in the subscript after the symbol "C" define the number of carbon atoms a particular group can contain.

The term "alkoxy" alone or as part of another group denotes an alkyl group as described above bonded through an oxygen linkage (—O—). Preferred alkoxy groups have from 1 to 8 carbon atoms. Examples of such groups include the methoxy, ethoxy, n-propoxy, isopropoxy, n-butoxy, isobutoxy, sec-butoxy, tert-butoxy, n-pentyloxy, isopentyloxy, n-hexyloxy, cyclohexyloxy, n-heptyloxy, n-octyloxy and 2-ethylhexyloxy.

The term "alkylthio" refers to an alkyl group as described above attached via a sulfur bridge. Preferred alkoxy and alkylthio groups are those in which an alkyl group is attached via the heteroatom bridge. Preferred alkylthio groups have from 1 to 8 carbon atoms. Examples of such groups include the methylthio, ethylthio, n-propythiol, n-butylthiol, and like.

The term "oxo," as used herein, refers to a keto (C=O) group. An oxo group that is a substituent of a nonaromatic carbon atom results in a conversion of —CH$_2$— to —C(=O)—.

The term "alkoxycarbonyl" herein alone or as part of another group denotes an alkoxy group bonded through a carbonyl group. An alkoxycarbonyl radical is represented by the formula: —C(O)OR, where the R group is a straight or branched C1-C6 alkyl group, cycloalkyl, aryl, or heteroaryl.

The term "alkylcarbonyl" herein alone or as part of another group denotes an alkyl group bonded through a carbonyl group. An alkoxycarbonyl radical is represented by the formula: —C(O)R, where the R group is a straight or branched C1-C6 alkyl group, cycloalkyl, aryl, or heteroaryl.

The term "alkanoyloxy" herein alone or as part of another group denotes an RCOO—group bonded through a single bond. An alkanoyloxy radical is represented by the formula RCOO—, where the R group is a straight or branched C1-C6 alkyl group, cycloalkyl, aryl, or heteroaryl.

The term "alkanoylamino" herein alone or as part of another group denotes an RCONH—group bonded through a single bond. An alkanoylamino radical is represented by the formula RCONH—, where the R group is a straight or branched C1-C6 alkyl group, cycloalkyl, aryl, or heteroaryl.

The term "arylalkyl" herein alone or as part of another group denotes an aromatic ring bonded through an alkyl group (such as benzyl) as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 20 atoms therein, with alternating (resonating) double bonds between adjacent carbon atoms or suitable heteroatoms. Aryl groups may optionally be substituted with one or more groups including, but not limited to halogen such as I, Br, F, or Cl; alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl S(O)$_m$ (m=0, 1, 2), or thiol.

The term "aromatic" refers to a cyclically conjugated molecular entity with a stability, due to delocalization, significantly greater than that of a hypothetical localized structure, such as the Kekule structure.

The term "amino" herein alone or as part of another group refers to —NH$_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "alkylsulfonyl" refers to groups of the formula (SO$_2$)-alkyl, in which the sulfur atom is the point of attachment. Preferably, alkylsulfonyl groups include C1-C6 alkylsulfonyl groups, which have from 1 to 6 carbon atoms. Methylsulfonyl is one representative alkylsulfonyl group.

The term "heteroatom" refers to any atom other than carbon, for example, N, O, or S.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (0, S or N) in at least one of the rings. Each ring of the heteroaryl group containing a heteroatom can contain one or two oxygen or sulfur atoms or from one to four nitrogen atoms provided that the total number of heteroatoms in each ring is four or less and each ring has at least one carbon atom.

The term "heterocyclic" or "heterocycloalkyl" herein alone or as part of another group refers to a cycloalkyl group (nonaromatic) in which one of the carbon atoms in the ring is replaced by a heteroatom selected from O, S or N. The "heterocycle" has from 1 to 3 fused, pendant or spiro rings, at least one of which is a heterocyclic ring (i.e., one or more ring atoms is a heteroatom, with the remaining ring atoms being carbon). The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy; lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. A heterocyclic group may generally be linked via any ring or substituent atom, provided that a stable compound results. N-linked heterocyclic groups are linked via a component nitrogen atom.

Typically, a heterocyclic ring comprises 1-4 heteroatoms; within certain embodiments each heterocyclic ring has 1 or 2 heteroatoms per ring. Each heterocyclic ring generally contains from 3 to 8 ring members (rings having from to 7 ring members are recited in certain embodiments), and heterocycles comprising fused, pendant or spiro rings typically contain from 9 to 14 ring members which consists of carbon atoms and contains one, two, or three heteroatoms selected from nitrogen, oxygen or sulfur. Examples of "heterocyclic" or "heterocycloalkyl" groups include piperazine, piperidine, morpholine, thiomorpholine, pyrrolidine, imidazolidine and thiazolide.

The term "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member.

The term "optionally substituted" as used herein means that the aryl, heterocyclyl, or other group may be substituted at one or more substitutable positions by one or more groups independently selected from alkyl (preferably lower alkyl), alkoxy (preferably lower alkoxy), nitro, monoalkylamino (preferably with one to six carbons), dialkylamino (preferably with one to six carbons), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy and lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

Optional substitution is also indicated by the phrase "substituted with from 0 to X substituents," where X is the maximum number of possible substituents. Certain optionally substituted groups are substituted with from 0 to 2, 3 or 4 independently selected substituents.

A dash ("-") that is not between two letters or symbols is used to indicate a point of the attachment for a substituent. For example, —CONH$_2$ is attached through the carbon atom. A dashed cycle that locates inside of a heterocyle ring is used to indicate a conjugated system. The bonds between two atoms may be single bond or double bond.

The term "protected" refers that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., Protective Groups in Organic Synthesis, John Wiley & Sons, New York (1999).

Depending on the particular purpose, it should also be recognized that contemplated compounds may be combined (in vivo, or in a pharmaceutical formulation or administration regimen) with at least one other pharmaceutically active agent to additively or synergistically provide a therapeutic pr prophylactic effect. Concentrations of second pharmaceutically active ingredients are typically at or preferably below those recommended for stand-alone administration, however, higher concentrations are also deemed suitable for use herein.

Therefore, contemplated pharmaceutical compositions will especially include those in which contemplated compounds (and optionally further pharmaceutically active ingredients) are provided with a suitable carrier, wherein contemplated compounds are preferably present at a concentration effective to treat or prevent a condition or disease associated with hyperuricemia.

The inventive subject matter also provides compounds, compositions and methods for manufacturing a pharmaceutical composition for treating a condition associated with hyperuricemia or gout. Contemplated methods can include formulating a oral formulation that contains a pharmaceutically acceptable carrier and a compound of Formula 1 or a pharmaceutically acceptable salt thereof:

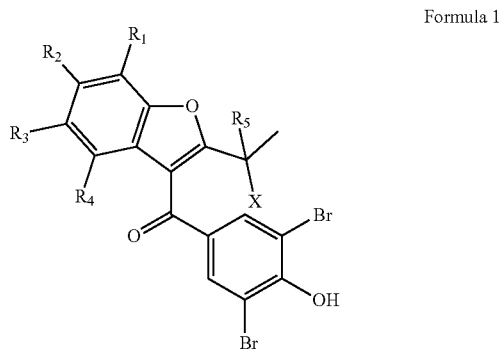

Formula 1

In such a compound or composition —X can be —OH, —OR, —OC(O)R, —NH$_3$+, —NO$_2$, —SO$_2$R, —CN, —SO$_3$H, —CHO, —COOH, —COCl, —CONH$_2$, —F, —Cl, —Br, or —I, where —R can be —H, —C$_1$-C$_{10}$ alkyl, or a —C$_1$-C$_{10}$ substituted alkyl; where —R$_2$ can be -deuterium or —H; and where —R$_1$, —R$_3$, —R$_4$ and —R$_5$ are each independently selected from —H, -deuterium, —F, —Cl, —Br, —I, —CN, —C$_1$-C$_6$-alkyl, C$_6$-C$_{14}$-aryl, substituted —C$_6$-C$_{14}$-aryl, C$_1$-C$_{14}$-alkoxy, -hydroxyl, -carboxyl, —C$_1$-C$_6$-alkylsulfonyl, -trifluoromethyl, —C$_1$-C$_6$-alkanoyloxy, —C$_1$-C$_6$-alkylthio, —C$_1$-C$_6$-alkylsulfonyl, —C$_2$-C$_6$-alkoxycarbonyl, —C$_2$-C$_6$-alkanoylamino, —O—R$_6$, —S$_2$R$_6$, —SO$_2$—R$_6$, —NHSO$_2$R$_6$, and —NHCO$_2$R$_6$, where —R$_6$ is phenyl or naphthyl, and can be optionally substituted with one to three groups selected from —C$_1$-C$_6$-alkyl, —C$_6$-C$_{10}$-aryl, —C$_1$-C$_6$-alkoxy and halogen, and —C$_4$-C$_{20}$-hydroxyheteroaryl, and where the heteroatoms in —C$_4$-C$_{20}$-hydroxyheteroaryl are nitrogen or oxygen.

The inventive subject matter also provides compounds, compositions and methods for manufacturing a pharmaceutical composition for treating a condition associated with hyperuricemia or gout. Some contemplated methods can include the step of formulating a oral formulation that contains a pharmaceutically acceptable carrier and a compound of Formula 1 or a pharmaceutically acceptable salt thereof:

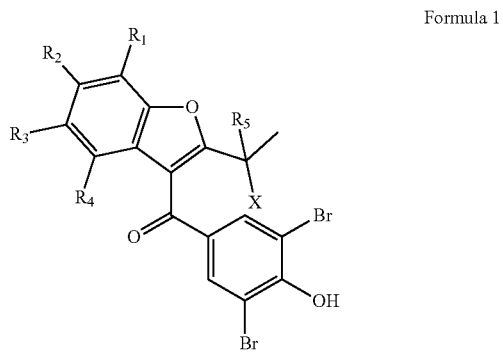

Formula 1

In such compounds or compositions —X can be —OH, —OR, —OC(O)R, —NH$_3$+, —NO$_2$, —SO$_2$R, —CN, —SO$_3$H, —CHO, —COOH, —COCl, —CONH$_2$, —F, —Cl, —Br, or —I, where —R can be —H, —C$_1$-C$_{10}$ alkyl, or a —C$_1$-C$_{10}$ substituted alkyl; where —R$_2$ can be -deuterium or —H; and where —R$_1$, —R$_3$, —R$_4$ and —R$_5$ are each independently selected from —H, -deuterium, —F, —Cl, —Br, —I, —CN, —C$_1$-C$_6$-alkyl, C$_6$-C$_{14}$-aryl, substituted —C$_6$-C$_{14}$-aryl, C$_1$-C$_{14}$-alkoxy, -hydroxyl, -carboxyl, —C$_1$-C$_6$-alkylsulfonyl, -trifluoromethyl, —C$_1$-C$_6$-alkanoyloxy, —C$_1$-C$_6$-alkylthio, —C$_1$-C$_6$-alkylsulfonyl, —C$_2$-C$_6$-alkoxycarbonyl, —C$_2$-C$_6$-alkanoylamino, —O—R$_6$, —S$_2$R$_6$, —SO$_2$—R$_6$, —NHSO$_2$R$_6$, and —NHCO$_2$R$_6$, where —R$_6$ can be phenyl or naphthyl, and can be optionally substituted with one to three groups selected from —C$_1$-C$_6$-alkyl, —C$_6$-C$_{10}$-aryl, —C$_1$-C$_6$-alkoxy and halogen, and —C$_4$-C$_{20}$-hydroxyheteroaryl, and wherein the heteroatoms in —C$_4$-C$_{20}$-hydroxyheteroaryl are selected from t nitrogen or oxygen; and where the compound of Formula 1 is present in a therapeutically effective amount to treat a condition associated with hyperuricemia.

Still further, the inventive subject matter also provides compounds, compositions and methods for inhibiting at least one kidney transporter responsible for uric acid reabsorption in renal tubules. Contemplated methods can include the step of administering a therapeutically effective amount of a compound of Formula 1, or a pharmaceutically acceptable salt thereof:

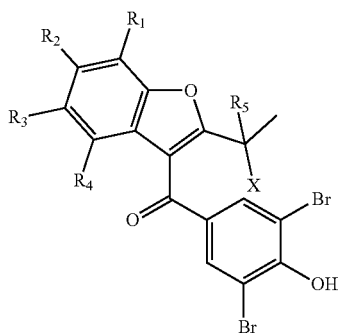

Formula 1

Wherein —X is —OH, —OR, —OC(O)R, —NH$_3$+, —NO$_2$, —SO$_2$R, —CN, —SO$_3$H, —CHO, —COOH, —COCl, —CONH$_2$, —F, —Cl, —Br or —I, wherein —R is a —H, —C$_1$-C$_{10}$ alkyl or a —C$_1$-C$_{10}$ substituted alkyl; wherein —R$_2$ is -deuterium or —H; and wherein —R$_1$, —R$_3$, —R$_4$ and —R$_5$ are each independently selected from a group consisting of —H, -deuterium, —F, —Cl, —Br, —I, —CN, —C$_1$-C$_6$-alkyl, C$_6$-C$_{14}$-aryl, substituted —C$_6$-C$_{14}$-aryl, C$_1$-C$_{14}$-alkoxy, -hydroxyl, -carboxyl, —C$_1$-C$_6$-alkylsulfonyl, -trifluoromethyl, —C$_1$-C$_6$-alkanoyloxy, —C$_1$-C$_6$-alkylthio, —C$_1$-C$_6$-alkylsulfonyl, —C$_2$-C$_6$-alkoxycarbonyl, —C$_2$-C$_6$-alkanoylamino, —O—R$_6$, —S$_2$R$_6$, —SO$_2$—R$_6$, —NHSO$_2$R$_6$ and —NHCO$_2$R$_6$, wherein —R$_6$ is phenyl or naphthyl, optionally substituted with one or three groups selected from —C$_1$-C$_6$-alkyl, —C$_6$-C$_{10}$-aryl, —C$_1$-C$_6$-alkoxy and halogen, and —C$_4$-C$_{20}$-hydroxyheteroaryl, and wherein the heteroatoms in —C$_4$-C$_{20}$-hydroxyheteroaryl are selected from the group consisting of nitrogen and oxygen.

In some contemplated embodiments, mediating renal reabsorption of uric acid comprises modulating at least one of URAT1 activity, OAT4 activity, and SGLT2 activity. Similarly, Inventors contemplate that a combined formulation that incorporates a compound of the inventive concept and one or more compound(s) that modulate(s) URAT1 activity, one or more compound(s) that modulate(s) OAT4 activity, and/or one or more compound(s) that modulate(s) SGLT2 activity, and that such a combined formulation can have utility in treating conditions disclosed herein.

The inventive subject matter also provides compounds, compositions and methods for treating a condition, disorder or disease mediated by at least one kidney transporter responsible for uric acid reabsorption in renal tubules. Contemplated methods can include the step of administering an effective amount of a composition comprising a pharmaceutically acceptable carrier and a compound of formula 1 or a pharmaceutically acceptable salt thereof.

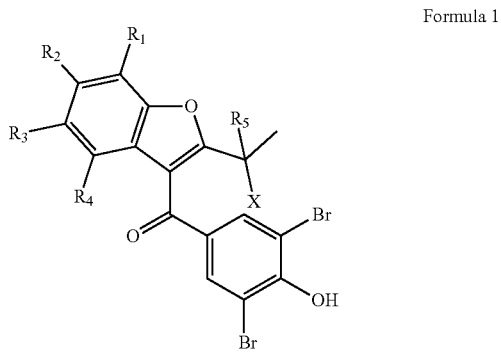

Formula 1

Wherein —X is —OH, —OR, —OC(O)R, —NH$_3$+, —NO$_2$, —SO$_2$R, —CN, —SO$_3$H, —CHO, —COOH, —COCl, —CONH$_2$, —F, —Cl, —Br or —I, wherein —R is a —H, —C$_1$-C$_{10}$ alkyl or a —C$_1$-C$_{10}$ substituted alkyl; wherein —R$_2$ is -deuterium or —H; and wherein —R$_1$, —R$_3$, —R$_4$ and —R$_5$ are each independently selected from a group consisting of —H, -deuterium, —F, —Cl, —Br, —I, —CN, —C$_1$-C$_6$-alkyl, C$_6$-C$_{14}$-aryl, substituted —C$_6$-C$_{14}$-aryl, C$_1$-C$_{14}$-alkoxy, -hydroxyl, -carboxyl, —C$_1$-C$_6$-alkylsulfonyl, -trifluoromethyl, —C$_1$-C$_6$-alkanoyloxy, —C$_1$-C$_6$-alkylthio, —C$_1$-C$_6$-alkylsulfonyl, —C$_2$-C$_6$-alkoxycarbonyl, —C$_2$-C$_6$-alkanoylamino, —O—R$_6$, —S$_2$R$_6$, —SO$_2$—R$_6$, —NHSO$_2$R$_6$ and —NHCO$_2$R$_6$, wherein —R$_6$ is phenyl or naphthyl, optionally substituted with one or three groups selected from —C$_1$-C$_6$-alkyl, —C$_6$-C$_{10}$-aryl, —C$_1$-C$_6$-alkoxy and halogen, and —C$_4$-C$_{20}$-hydroxyheteroaryl, and wherein the heteroatoms in —C$_4$-C$_{20}$-hydroxyheteroaryl are selected from the group consisting of nitrogen and oxygen.

The inventive subject matter also provides compounds of Formula 1, or a pharmaceutically acceptable salt thereof:

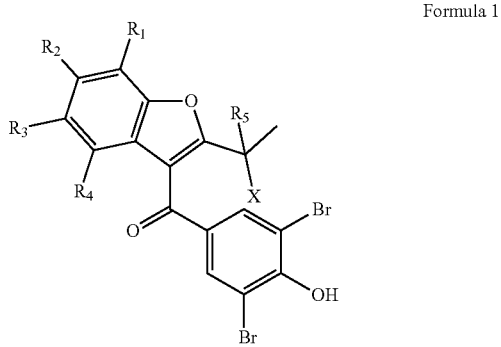

Formula 1

In such a compound —X can be —OH, —OR, —OC(O)R, —NH$_3$+, —NO$_2$, —SO$_2$R, —CN, —SO$_3$H, —CHO, —COOH, —COCl, —CONH$_2$, —F, —Cl, —Br, or —I, where —R can be —H, —C$_1$-C$_{10}$ alkyl or a —C$_1$-C$_{10}$ substituted alkyl; where —R$_2$ can be -deuterium or —H; and where —R$_1$, —R$_3$, —R$_4$ and —R$_5$ are each independently selected from —H, -deuterium, —F, —Cl, —Br, —I, —CN, —C$_1$-C$_6$-alkyl, C$_6$-C$_{14}$-aryl, substituted —C$_6$-C$_{14}$-aryl, C$_1$-C$_{14}$-alkoxy, -hydroxyl, -carboxyl, —C$_1$-C$_6$-alkylsulfonyl, -trifluoromethyl, —C$_1$-C$_6$-alkanoyloxy, —C$_1$-C$_6$-alkylthio, —C$_1$-C$_6$-alkylsulfonyl, —C$_2$-C$_6$-alkoxycarbonyl, —C$_2$-C$_6$-alkanoylamino, —O—R$_6$, —S$_2$R$_6$, —SO$_2$—R$_6$, —NHSO$_2$R$_6$, and —NHCO$_2$R$_6$, where —R$_6$ can be phenyl or naphthyl, and can be optionally substituted with one to three groups selected from —C$_1$-C$_6$-alkyl, —C$_6$-C$_{10}$-aryl, —C$_1$-C$_6$-alkoxy and halogen, and —C$_4$-C$_{20}$-hydroxyheteroaryl, and where the heteroatoms in —C$_4$-C$_{20}$-hydroxyheteroaryl are nitrogen or oxygen.

The inventive subject matter also provides use of the compound set forth above in the manufacture of a drug. In some contemplated embodiments, the compound is present in an amount effective to treat a condition associated with hyperuricemia or gout. The compound set forth above can also be used to treat a condition associated with hyperuricemia. Alternatively or additionally, the compound set forth above can be used to modulate URAT1 activity in a person. Still further, it is also contemplated that the compound set forth above can be used to treat or prevent a disorder or disease mediated by URAT1 activity.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Also, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Thus, specific, compounds, compositions and methods for treating hyperuricemia or gout have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

The invention claimed is:

1. A compound of Formula 1, or a pharmaceutically acceptable salt thereof, wherein:

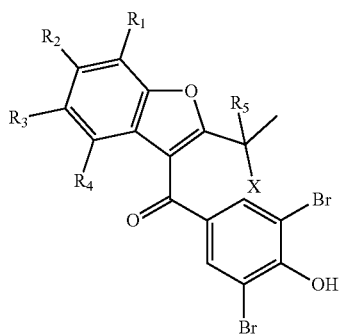

Formula 1

—X is —OH, —F, or —Cl;
wherein —R$_1$, —R$_2$, —R$_3$, —R$_4$ and —R$_5$ are each independently selected from a group consisting of —H, -deuterium, —F, —Cl, —C$_1$-C$_6$-alkyl, and -hydroxyl; and
wherein at least one of —R$_1$, —R$_2$, —R$_3$, —R$_4$ and —R$_5$ is -deuterium.

2. The compound of claim 1, wherein X is —OH.
3. The compound of claim 2 wherein —R$_5$ is —H.
4. The compound of claim 1, wherein X is —F.
5. The compound of claim 4 wherein —R$_5$ is —H.
6. A pharmaceutical composition comprising:
a pharmaceutically acceptable carrier and
a compound of claim 1, or a pharmaceutically acceptable salt thereof.
7. A method of treating hyperuricemia or gout in a mammal, comprising administering to the mammal a therapeutically effective amount of a compound of claim 1, or a pharmaceutically acceptable salt thereof.
8. The method of claim 7, wherein the composition further comprises a xanthine oxidase inhibitor.
9. The method of claim 8, wherein the xanthine oxidase inhibitor is allopurinol oxypurinol, febuxostat, topiroxostat, or inositol.

* * * * *